US006127180A

United States Patent [19]
Narva et al.

[11] Patent Number: 6,127,180
[45] Date of Patent: *Oct. 3, 2000

[54] PESTICIDAL TOXINS

[75] Inventors: Kenneth E. Narva; H. Ernest Schnepf, both of San Diego; Mark Knuth, Poway, all of Calif.; Michael R. Pollard, Okemos, Mich.; Guy Cardineau, Poway, Calif.; George E. Schwab, Encinitas, Calif.; Tracy Ellis Michaels, Escondido, Calif.

[73] Assignee: Mycogen Corporation, San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/844,188

[22] Filed: Apr. 18, 1997

Related U.S. Application Data

[63] Continuation-in-part of application No. 08/633,993, Apr. 19, 1996.

[51] Int. Cl.$^7$ .............................. C12N 15/32; C12N 1/21; C12N 5/10; C07K 14/325
[52] U.S. Cl. ..................... 435/419; 536/23.71; 536/23.1; 435/252.3; 435/254.2; 435/320.1; 800/301
[58] Field of Search ................................ 536/23.71, 23.1; 435/252.3, 419, 254.2, 320.1; 800/30

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Herrnstadt et al. | 424/84 |
| 4,849,217 | 7/1989 | Soares et al. | 424/93 |
| 4,853,331 | 8/1989 | Herrnstadt et al. | 435/252.1 |
| 4,918,006 | 4/1990 | Ellar et al. | 435/69.1 |
| 4,948,734 | 8/1990 | Edwards et al. | 435/252.5 |
| 5,151,363 | 9/1992 | Payne | 435/252.5 |
| 5,204,100 | 4/1993 | Carozzi et al. | 424/932 |
| 5,208,017 | 5/1993 | Bradfish et al. | 494/84 |

FOREIGN PATENT DOCUMENTS

| | | |
|---|---|---|
| 0359472 | 3/1990 | European Pat. Off. . |
| 454 485 | 10/1991 | European Pat. Off. . |
| 0462721 | 12/1991 | European Pat. Off. . |
| 94/16079 | 7/1994 | WIPO . |
| 9416079 | 7/1994 | WIPO . |
| 9502694 | 1/1995 | WIPO . |

OTHER PUBLICATIONS

Beegle, C.C. (1978) "Use of Entomogenous Bacteria in Agroecosystems" Developments in Industrial Microbiologu 20:97–104.

Couch, T.L. (1980) "Mosquito Pathogenicity of *Bacillus thuringiensis* var. *israelensis*" Developments in Industrial Microbiology 22:61–76.

Feitelson, J.S. et al. (1992) "*Bacillus thuringiensis*: Insects and Beyond" Bio/Technology 10:271–275.

Gaertner, F.H. (1989) "Cellular Delivery Systems for Insecticidal Proteins: Living and Non–Living Microorganisms" Controlled Delivery of Crop–Protection Agents, pp. 245–257.

Gaertner, F., L. Kim (1988) "Current Applied Recombinant DNA Projects" Tibtech 6(4):S4–S7.

Hofte, H., H.R. Whiteley (1989) "Insecticidal Crystal Proteins of *Bacillus thuringiensis*" Microbiological Reviews 53(2):242–255.

Krieg, V.A. et al. (1983) "*Bacillus thuringiensis* var. *tenebrionis*: A New Pathotype Effective Against Larvae of Coleoptera" Z. ang. Ent. 96:500–508.

Schnepf, H.E., H.R. Whiteley (1981) "Cloning and expression of the *Bacillus thuringiensis* crystal protein gene in *Escherichia coli*" Proc. Natl. Acad. Sci. USA 78(5):2893–2897.

*Primary Examiner*—Rebecca E. Prouty
*Attorney, Agent, or Firm*—Saliwanchik, Lloyd & Saliwanchik

[57] ABSTRACT

The subject invention concerns new classes of pesticidal toxins and the polynucleotide sequences which encode these toxins. Also described are novel pesticidal isolates of *Bacillus thuringiensis*.

119 Claims, 3 Drawing Sheets

```
            1                                                                  50
{149b145k}  .........    .....GLYAA  TYLSLDDSGV  SLMNKNDDDI  DDYNLKWFLF
{167h245k}  .........    .....HAA    TYLSLDDSGV  SLMNKNDDDI  DDYNLRWFLF
{80jj145k}  MLDTNKVYEI   SNLANGLYTS  TYLSLDDSGV  SLMSKKDEDI  DDYNLKWELF
Consensus   ---------    ----------  TYLSLDDSGV  SLM-K-D-DI  DDYNL-WELF 51                                                                 100
{149b145k}  PIDDDQYIIT   SYAANNCKVW  NVNNDKINVS  TYSSTNSIQK  WQIKANGSSY
{167h245k}  PIDDNQYIIT   SYAANNCKVW  NVNNDKINVS  TYSSTNSIQK  WQIKANASSY
{80jj145k}  PIDNNQYIIT   SYGANNCKVW  NVKNDKINVS  TYSSTNSVQK  WQIKAKDSSY
Consensus   PID--QYIIT   SY-ANNCKVW  NV-NDKINVS  TYSSTNS-QK  WQIKA--SSY 101                                                                150
{149b145k}  VIQSDNGKVL   TAGTGQALGL  IRLTDESSNN  PNQQWNLTSV  QTIQLPQKPI
{167h245k}  VIQSNNGKVL   TAGTGQSLGL  IRLTDESPDN  PNQQWNLTPV  QTIQLPPKPT
{80jj145k}  IIQSDNGKVL   TAGVGQSLGI  VRLTDEFPEN  SNQQWNLTPV  QTIQLPQKPK
Consensus   -IQS-NGKVL   TAG-GQ-LG-  -RLTDE---N  -NQQWNLT-V  QTIQLP-KP- 151                                                                200
{149b145k}  IDTKLKDYPK   YSPTGNIDNG  TSPQLMGWTL  VPCIMVNDPN  IDKNTQIKTT
{167h245k}  IDTKLKDYPK   YSQTGNIDKG  TPPQLMGWTL  IPCIMVNDPN  IDKNTQIKTT
{80jj145k}  IDEKLKDHPE   YSETGNINPK  TTPQLMGWTL  VPCIMVNDSK  IDKNTQIKTT
Consensus   ID-KLKD-P-   YS-TGNI---  T-PQLMGWTL  --PCIMVND--  IDKNTQIKTT
```

FIG. 1A

```
              201                                                          250
{149b145k}    PYYILKKYQY    WQRAVGSNVA    LRPHEKKSYT    YEWGTEIDQK    TTIINTLGFQ
{167h245k}    PYYILKKYQY    WQQAVGSNVA    LRPHEKKSYA    YEWGTEIDQK    TTIINTLGFQ
{80jj145k}    PYYIFKKYKY    WNLAKGSNVS    LLPHQKRSYD    YEWGTEKNQK    TTIINTVGLQ
Consensus     PYYI-KKY-Y    W--A-GSNV-    L-PH-K-SY-    YEWGTE--QK    TTIINT-G-Q 251                                                          300
{149b145k}    INIDSGMKFD    IPEVGGGTDE    IKTQLNEELK    IEYSHETKIM    EKY.......
{167h245k}    INIDSGMKFD    IPEVGGGTDE    IKTQLNEELK    IEYSRETKIM    EKY.......
{80jj145k}    INIDSGMKFE    VPEVGGGTED    IKTQLTEELK    VEYSTETKIM    TKYQEHSEID
Consensus     INIDSGMKF-    -PEVGGGT--    IKTQL-EELK    -EYS-ETKIM    -KY-------

301                                                          350
{149b145k}    ..........    ..........    ..........    ..........    ..........
{167h245k}    ..........    ..........    ..........    ..........    ..........
{80jj145k}    NPTNQPMNSI    GLLIYTSLEL    YRYNGTEIKI    MDIETSDHDT    YTLTSYPNHK
Consensus     ----------    ----------    ----------    ----------    ----------

351                         386
{149b145k}    ..........    ..........    ......
{167h245k}    ..........    ..........    ......
{80jj145k}    EALLLLTNHS    YEEVEEITKI    PKHTLIKLKK    HYFKK.
Consensus     ----------    ----------    ------
```

FIG. 1B

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Met Leu Asp Thr Asn
1              5

(2) INFORMATION FOR SEQ ID NO:2:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Leu Asp Thr Asn Lys Val Tyr Glu Ile Ser Asn Leu Ala Asn Gly
1              5                    10                  15

Leu Tyr Thr Ser Thr Tyr Leu Ser Leu
            20                   25

(2) INFORMATION FOR SEQ ID NO:3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Ser Ala Arg Glu Val His Ile Glu Ile Asn Asn Thr Arg His Thr Leu
1              5                    10                  15

Gln Leu Glu Ala Lys Thr Lys Leu
            20

(2) INFORMATION FOR SEQ ID NO:4:

(i) SEQUENCE CHARACTERISTICS:
        (A) LENGTH: 25 amino acids
        (B) TYPE: amino acid

```
            (C) STRANDEDNESS: single
            (D) TOPOLOGY: linear (ii) MOLECULE TYPE: protein (xi) SEQUENCE DESCRIPTION: SEQ ID NO:4:

Met Leu Asp Thr Asn Lys Val Tyr Glu Ile Ser Asn His Ala Asn Gly
1               5                   10                  15

Leu Tyr Ala Ala Thr Tyr Leu Ser Leu
            20                  25

(2) INFORMATION FOR SEQ ID NO:5:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Ser Ala Arg Glu Val His Ile Asp Val Asn Asn Lys Thr Gly His Thr
1               5                   10                  15

Leu Gln Leu Glu Asp Lys Thr Lys Leu Asp Gly Gly Arg Trp Arg Thr
            20                  25                  30

Ser Pro Xaa Asn Val Ala Asn Asp Gln Ile Lys Thr Phe Val Ala Glu
        35                  40                  45

Ser Asn
    50

(2) INFORMATION FOR SEQ ID NO:6:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Leu Asp Thr Asn Lys Ile Tyr Glu Ile Ser Asn Tyr Ala Asn Gly
1               5                   10                  15

Leu His Ala Ala Thr Tyr Leu Ser Leu
            20                  25

(2) INFORMATION FOR SEQ ID NO:7:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ser Ala Arg Glu Val His Ile Asp Val Asn Asn Lys Thr Gly His Thr
1               5                   10                  15

Leu Gln Leu Glu Asp Lys Thr Lys Leu
            20                  25

(2) INFORMATION FOR SEQ ID NO:8:
```

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

ATGNTNGATA CNAATAAAGT NTATGAAAT                                          29

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

GGATTATCTA TCTCTGAGTG TTCTTG                                             26

(2) INFORMATION FOR SEQ ID NO:10:

(i) SEQUENCE CHARACTERISTICS:
        (A) LENGTH: 1158 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATGTTAGATA CTAATAAAGT TTATGAAATA AGCAATCTTG CTAATGGATT ATATACATCA         60

ACTTATTTAA GTCTTGATGA TTCAGGTGTT AGTTTAATGA GTAAAAAGGA TGAAGATATT        120

GATGATTACA ATTTAAAATG GTTTTTATTT CCTATTGATA ATAATCAATA TATTATTACA        180

AGCTATGGAG CTAATAATTG TAAAGTTTGG AATGTTAAAA ATGATAAAAT AAATGTTTCA        240

ACTTATTCTT CAACAAACTC TGTACAAAAA TGGCAAATAA AAGCTAAAGA TTCTTCATAT        300

ATAATACAAA GTGATAATGG AAAGGTCTTA ACAGCAGGAG TAGGTCAATC TCTTGGAATA        360

GTACGCCTAA CTGATGAATT TCCAGAGAAT TCTAACCAAC AATGGAATTT AACTCCTGTA        420

CAAACAATTC AACTCCCACA AAAACCTAAA ATAGATGAAA AATTAAAAGA TCATCCTGAA        480

TATTCAGAAA CCGGAAATAT AAATCCTAAA ACAACTCCTC AATTAATGGG ATGGACATTA        540

GTACCTTGTA TTATGGTAAA TGATTCAAAA ATAGATAAAA ACACTCAAAT TAAAACTACT        600

CCATATTATA TTTTTAAAAA ATATAAATAC TGGAATCTAG CAAAAGGAAG TAATGTATCT        660

TTACTTCCAC ATCAAAAAAG ATCATATGAT TATGAATGGG GTACAGAAAA AAATCAAAAA        720

ACAACTATTA TTAATACAGT AGGATTGCAA ATTAATATAG ATTCAGGAAT GAAATTTGAA        780

GTACCAGAAG TAGGAGGAGG TACAGAAGAC ATAAAAACAC AATTAACTGA AGAATTAAAA        840

GTTGAATATA GCACTGAAAC CAAAATAATG ACGAAATATC AAGAACACTC AGAGATAGAT        900

AATCCAACTA ATCAACCAAT GAATTCTATA GGACTTCTTA TTTATACTTC TTTAGAATTA        960

TATCGATATA ACGGTACAGA AATTAAGATA ATGGACATAG AAACTTCAGA TCATGATACT       1020

TACACTCTTA CTTCTTATCC AAATCATAAA GAAGCATTAT TACTTCTCAC AAACCATTCG       1080

TATGAAGAAG TAGAAGAAAT AACAAAAATA CCTAAGCATA CACTTATAAA ATTGAAAAAA       1140

CATTATTTTA AAAAATAA                                                    1158

(2) INFORMATION FOR SEQ ID NO:11:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Met Leu Asp Thr Asn Lys Val Tyr Glu Ile Ser Asn Leu Ala Asn Gly
1               5                   10                  15

Leu Tyr Thr Ser Thr Tyr Leu Ser Leu Asp Asp Ser Gly Val Ser Leu
            20                  25                  30

Met Ser Lys Lys Asp Glu Asp Ile Asp Asp Tyr Asn Leu Lys Trp Phe
        35                  40                  45

Leu Phe Pro Ile Asp Asn Asn Gln Tyr Ile Ile Thr Ser Tyr Gly Ala
    50                  55                  60

Asn Asn Cys Lys Val Trp Asn Val Lys Asn Asp Lys Ile Asn Val Ser
65                  70                  75                  80

Thr Tyr Ser Ser Thr Asn Ser Val Gln Lys Trp Gln Ile Lys Ala Lys
                85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350
```

Leu Leu Leu Leu Thr Asn His Ser Tyr Glu Val Glu Glu Ile Thr
            355                 360                 365

Lys Ile Pro Lys His Thr Leu Ile Lys Leu Lys Lys His Tyr Phe Lys
        370                 375                 380

Lys
385

(2) INFORMATION FOR SEQ ID NO:12:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGACTATATG CAGCAACTTA TTTAAGTTTA GATGATTCAG GTGTTAGTTT AATGAATAAA      60

AATGATGATG ATATTGATGA TTATAACTTA AAATGGTTTT TATTTCCTAT TGATGATGAT     120

CAATATATTA TTACAAGCTA TGCAGCAAAT AATTGTAAAG TTTGGAATGT TAATAATGAT     180

AAAATAAATG TTTCGACTTA TTCTTCAACA AATTCAATAC AAAAATGGCA AATAAAAGCT     240

AATGGTTCTT CATATGTAAT ACAAAGTGAT AATGGAAAAG TCTTAACAGC AGGAACCGGT     300

CAAGCTCTTG GATTGATACG TTTAACTGAT GAATCCTCAA ATAATCCCAA TCAACAATGG     360

AATTTAACTT CTGTACAAAC AATTCAACTT CCACAAAAAC CTATAATAGA TACAAAATTA     420

AAAGATTATC CCAAATATTC ACCAACTGGA ATATAGATA ATGGAACATC TCCTCAATTA     480

ATGGGATGGA CATTAGTACC TTGTATTATG GTAAATGATC CAAATATAGA TAAAAATACT     540

CAAATTAAAA CTACTCCATA TTATATTTTA AAAAAATATC AATATTGGCA ACGAGCAGTA     600

GGAAGTAATG TAGCTTTACG TCCACATGAA AAAAAATCAT ATACTTATGA ATGGGGCACA     660

GAAATAGATC AAAAAACAAC AATTATAAAT ACATTAGGAT TCAAATCAA TATAGATTCA     720

GGAATGAAAT TTGATATACC AGAAGTAGGT GGAGGTACAG ATGAAATAAA AACACAACTA     780

AATGAAGAAT TAAAAATAGA ATATAGTCAT GAAACTAAAA TAATGGAAAA ATAT           834

(2) INFORMATION FOR SEQ ID NO:13:

(i) SEQUENCE CHARACTERISTICS:
        (A) LENGTH: 278 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Gly Leu Tyr Ala Ala Thr Tyr Leu Ser Leu Asp Asp Ser Gly Val Ser
1               5                   10                  15

Leu Met Asn Lys Asn Asp Asp Ile Asp Asp Tyr Asn Leu Lys Trp
            20                  25                  30

Phe Leu Phe Pro Ile Asp Asp Gln Tyr Ile Ile Thr Ser Tyr Ala
        35                  40                  45

Ala Asn Asn Cys Lys Val Trp Asn Val Asn Asn Asp Lys Ile Asn Val
    50                  55                  60

Ser Thr Tyr Ser Ser Thr Asn Ser Ile Gln Lys Trp Gln Ile Lys Ala
65                  70                  75                  80

```
Asn Gly Ser Ser Tyr Val Ile Gln Ser Asp Asn Gly Lys Val Leu Thr
            85                  90                  95

Ala Gly Thr Gly Gln Ala Leu Gly Leu Ile Arg Leu Thr Asp Glu Ser
        100                 105                 110

Ser Asn Asn Pro Asn Gln Gln Trp Asn Leu Thr Ser Val Gln Thr Ile
        115                 120                 125

Gln Leu Pro Gln Lys Pro Ile Ile Asp Thr Lys Leu Lys Asp Tyr Pro
    130                 135                 140

Lys Tyr Ser Pro Thr Gly Asn Ile Asp Asn Gly Thr Ser Pro Gln Leu
145                 150                 155                 160

Met Gly Trp Thr Leu Val Pro Cys Ile Met Val Asn Asp Pro Asn Ile
            165                 170                 175

Asp Lys Asn Thr Gln Ile Lys Thr Thr Pro Tyr Tyr Ile Leu Lys Lys
        180                 185                 190

Tyr Gln Tyr Trp Gln Arg Ala Val Gly Ser Asn Val Ala Leu Arg Pro
        195                 200                 205

His Glu Lys Lys Ser Tyr Thr Tyr Glu Trp Gly Thr Glu Ile Asp Gln
    210                 215                 220

Lys Thr Thr Ile Ile Asn Thr Leu Gly Phe Gln Ile Asn Ile Asp Ser
225                 230                 235                 240

Gly Met Lys Phe Asp Ile Pro Glu Val Gly Gly Thr Asp Glu Ile
            245                 250                 255

Lys Thr Gln Leu Asn Glu Glu Leu Lys Ile Glu Tyr Ser His Glu Thr
        260                 265                 270

Lys Ile Met Glu Lys Tyr
        275

(2) INFORMATION FOR SEQ ID NO:14:

(i) SEQUENCE CHARACTERISTICS:
        (A) LENGTH: 829 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

ACATGCAGCA ACTTATTTAA GTTTAGATGA TTCAGGTGTT AGTTTAATGA ATAAAAATGA      60

TGATGATATT GATGACTATA ATTTAAGGTG GTTTTTATTT CCTATTGATG ATAATCAATA     120

TATTATTACA AGCTACGCAG CGAATAATTG TAAGGTTTGG AATGTTAATA ATGATAAAAT     180

AAATGTTTCA ACTTATTCTT CAACAAACTC GATACAGAAA TGGCAAATAA AAGCTAATGC     240

TTCTTCGTAT GTAATACAAA GTAATAATGG GAAAGTTCTA ACAGCAGGAA CCGGTCAATC     300

TCTTGGATTA ATACGTTTAA CGGATGAATC ACCAGATAAT CCCAATCAAC AATGGAATTT     360

AACTCCTGTA CAAACAATTC AACTCCCACC AAAACCTACA ATAGATACAA AGTTAAAAGA     420

TTACCCCAAA TATTCACAAA CTGGCAATAT AGACAAGGGA ACACCTCCTC AATTAATGGG     480

ATGGACATTA ATACCTTGTA TTATGGTAAA TGATCCCAAT ATAGATAAAA ACACTCAAAT     540

CAAAACTACT CCATATTATA TTTTAAAAAA ATATCAATAT TGGCAACAAG CAGTAGGAAG     600

TAATGTAGCT TTACGTCCGC ATGAAAAAAA ATCATATGCT TATGAGTGGG GTACAGAAAT     660

AGATCAAAAA ACAACTATCA TTAATACATT AGGATTTCAG ATTAATATAG ATTCGGGAAT     720

GAAATTTGAT ATACCAGAAG TAGGTGGAGG TACAGATGAA ATAAAAACAC AATTAAACGA     780

AGAATTAAAA ATAGAATATA GCCGTGAAAC CAAAATAATG GAAAAATAT                829
```

(2) INFORMATION FOR SEQ ID NO:15:

(i) SEQUENCE CHARACTERISTICS:
        (A) LENGTH: 276 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
His Ala Ala Thr Tyr Leu Ser Leu Asp Asp Ser Gly Val Ser Leu Met
  1               5                  10                  15

Asn Lys Asn Asp Asp Asp Ile Asp Asp Tyr Asn Leu Arg Trp Phe Leu
             20                  25                  30

Phe Pro Ile Asp Asp Asn Gln Tyr Ile Ile Thr Ser Tyr Ala Ala Asn
             35                  40                  45

Asn Cys Lys Val Trp Asn Val Asn Asp Lys Ile Asn Val Ser Thr
 50                  55                  60

Tyr Ser Ser Thr Asn Ser Ile Gln Lys Trp Gln Ile Lys Ala Asn Ala
 65                  70                  75                  80

Ser Ser Tyr Val Ile Gln Ser Asn Asn Gly Lys Val Leu Thr Ala Gly
                     85                  90                  95

Thr Gly Gln Ser Leu Gly Leu Ile Arg Leu Thr Asp Glu Ser Pro Asp
                 100                 105                 110

Asn Pro Asn Gln Gln Trp Asn Leu Thr Pro Val Gln Thr Ile Gln Leu
             115                 120                 125

Pro Pro Lys Pro Thr Ile Asp Thr Lys Leu Lys Asp Tyr Pro Lys Tyr
             130                 135                 140

Ser Gln Thr Gly Asn Ile Asp Lys Gly Thr Pro Pro Gln Leu Met Gly
145                 150                 155                 160

Trp Thr Leu Ile Pro Cys Ile Met Val Asn Asp Pro Asn Ile Asp Lys
                 165                 170                 175

Asn Thr Gln Ile Lys Thr Thr Pro Tyr Tyr Ile Leu Lys Lys Tyr Gln
             180                 185                 190

Tyr Trp Gln Gln Ala Val Gly Ser Asn Val Ala Leu Arg Pro His Glu
             195                 200                 205

Lys Lys Ser Tyr Ala Tyr Glu Trp Gly Thr Glu Ile Asp Gln Lys Thr
210                 215                 220

Thr Ile Ile Asn Thr Leu Gly Phe Gln Ile Asn Ile Asp Ser Gly Met
225                 230                 235                 240

Lys Phe Asp Ile Pro Glu Val Gly Gly Gly Thr Asp Glu Ile Lys Thr
                 245                 250                 255

Gln Leu Asn Glu Glu Leu Lys Ile Glu Tyr Ser Arg Glu Thr Lys Ile
             260                 265                 270

Met Glu Lys Tyr
         275
```

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Asp Ile Asp Asp Tyr Asn Leu
1               5

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Trp Phe Leu Phe Pro Ile Asp
1               5

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Gln Ile Lys Thr Thr Pro Tyr Tyr
1               5

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Tyr Glu Trp Gly Thr Glu
1               5

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:20:

GATATNGATG ANTAYAAYTT N                                      21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:21:

TGGTTTTTNT TTCCNATNGA N                                              21

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:22:

CAAATNAAAA CNACNCCATA TTAT                                           24

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:23:

TANGANTGGG GNACAGAA                                                  18

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:24:

ATAATATGGN GTNGTTTTNA TTTG                                           24

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:25:

TTCTGTNCCC CANTCNTA                                                  18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:26:

CTCAAAGCGG ATCAGGAG                                                  18

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:27:

```
GCGTATTCGG ATATGCTTGG                                              20
```

(2) INFORMATION FOR SEQ ID NO:28:

(i) SEQUENCE CHARACTERISTICS:
        (A) LENGTH: 386 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Thr Tyr Leu Ser Leu Asp Asp Ser Gly Val Ser Leu
            20                  25                  30

Met Xaa Lys Xaa Asp Xaa Asp Ile Asp Asp Tyr Asn Leu Xaa Trp Phe
        35                  40                  45

Leu Phe Pro Ile Asp Xaa Xaa Gln Tyr Ile Ile Thr Ser Tyr Xaa Ala
50                  55                  60

Asn Asn Cys Lys Val Trp Asn Val Xaa Asn Asp Lys Ile Asn Val Ser
65                  70                  75                  80

Thr Tyr Ser Ser Thr Asn Ser Xaa Gln Lys Trp Gln Ile Lys Ala Xaa
                85                  90                  95

Xaa Ser Ser Tyr Xaa Ile Gln Ser Xaa Asn Gly Lys Val Leu Thr Ala
            100                 105                 110

Gly Xaa Gly Gln Xaa Leu Gly Xaa Xaa Arg Leu Thr Asp Glu Xaa Xaa
        115                 120                 125

Xaa Asn Xaa Asn Gln Gln Trp Asn Leu Thr Xaa Val Gln Thr Ile Gln
130                 135                 140

Leu Pro Xaa Lys Pro Xaa Ile Asp Xaa Lys Leu Lys Asp Xaa Pro Xaa
145                 150                 155                 160

Tyr Ser Xaa Thr Gly Asn Ile Xaa Xaa Xaa Thr Xaa Pro Gln Leu Met
                165                 170                 175

Gly Trp Thr Leu Xaa Pro Cys Ile Met Val Asn Asp Xaa Xaa Ile Asp
            180                 185                 190

Lys Asn Thr Gln Ile Lys Thr Thr Pro Tyr Tyr Ile Xaa Lys Lys Tyr
        195                 200                 205

Xaa Tyr Trp Xaa Xaa Ala Xaa Gly Ser Asn Val Xaa Leu Xaa Pro His
210                 215                 220

Xaa Lys Xaa Ser Tyr Xaa Tyr Glu Trp Gly Thr Glu Xaa Xaa Gln Lys
225                 230                 235                 240

Thr Thr Ile Ile Asn Thr Xaa Gly Xaa Gln Ile Asn Ile Asp Ser Gly
                245                 250                 255

Met Lys Phe Xaa Xaa Pro Glu Val Gly Gly Gly Thr Xaa Xaa Ile Lys
            260                 265                 270
```

```
Thr Gln Leu Xaa Glu Glu Leu Lys Xaa Glu Tyr Ser Xaa Glu Thr Lys
            275                 280                 285

Ile Met Xaa Lys Tyr Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa
            370                 375                 380

Xaa Xaa
385
```

(2) INFORMATION FOR SEQ ID NO:29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:29:

```
GNGAAGTNCA TATNGAAATN AATAATAC                                 28
```

(2) INFORMATION FOR SEQ ID NO:30:

(i) SEQUENCE CHARACTERISTICS:
        (A) LENGTH: 2015 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
ATTAATTTTA TGGAGGTTGA TATTTATGTC AGCTCGCGAA GTACACATTG AAATAAACAA    60

TAAAACACGT CATACATTAC AATTAGAGGA TAAAACTAAA CTTAGCGGCG GTAGATGGCG   120

AACATCACCT ACAAATGTTG CTCGTGATAC AATTAAAACA TTTGTAGCAG AATCACATGG   180

TTTTATGACA GGAGTAGAAG GTATTATATA TTTTAGTGTA AACGGAGACG CAGAAATTAG   240

TTTACATTTT GACAATCCTT ATATAGGTTC TAATAAATGT GATGGTTCTT CTGATAAACC   300

TGAATATGAA GTTATTACTC AAAGCGGATC AGGAGATAAA TCTCATGTGA CATATACTAT   360

TCAGACAGTA TCTTTACGAT TATAAGGAAA ATTTATAAAA ACTGTATTTT TTACTAAAAT   420

ACCAAAAAAT ACATATTTAT TTTTTGGTAT TTTCTAATAT GAAATATGAA TTATAAAAAT   480

ATTAATAAAA AAGGTGATAA AAATTATGTT AGATACTAAT AAAGTTTATG AAATAAGCAA   540

TCTTGCTAAT GGATTATATA CATCAACTTA TTTAAGTCTT GATGATTCAG GTGTTAGTTT   600

AATGAGTAAA AAGGATGAAG ATATTGATGA TTACAATTTA AAATGGTTTT TATTTCCTAT   660

TGATAATAAT CAATATATTA TTACAAGCTA TGGAGCTAAT AATTGTAAAG TTTGGAATGT   720

TAAAAATGAT AAAATAAATG TTTCAACTTA TTCTTCAACA AACTCTGTAC AAAAATGGCA   780

AATAAAAGCT AAAGATTCTT CATATATAAT ACAAAGTGAT AATGGAAAGG TCTTAACAGC   840
```

```
AGGAGTAGGT CAATCTCTTG GAATAGTACG CCTAACTGAT GAATTTCCAG AGAATTCTAA      900

CCAACAATGG AATTTAACTC CTGTACAAAC AATTCAACTC CCACAAAAAC CTAAAATAGA      960

TGAAAAATTA AAAGATCATC CTGAATATTC AGAAACCGGA AATATAAATC CTAAAACAAC     1020

TCCTCAATTA ATGGGATGGA CATTAGTACC TTGTATTATG GTAAATGATT CAAAAATAGA     1080

TAAAAACACT CAAATTAAAA CTACTCCATA TTATATTTTT AAAAAATATA AATACTGGAA     1140

TCTAGCAAAA GGAAGTAATG TATCTTTACT TCCACATCAA AAAAGATCAT ATGATTATGA     1200

ATGGGGTACA GAAAAAAATC AAAAAACAAC TATTATTAAT ACAGTAGGAT TGCAAATTAA     1260

TATAGATTCA GGAATGAAAT TTGAAGTACC AGAAGTAGGA GGAGGTACAG AAGACATAAA     1320

AACACAATTA ACTGAAGAAT TAAAAGTTGA ATATAGCACT GAAACCAAAA TAATGACGAA     1380

ATATCAAGAA CACTCAGAGA TAGATAATCC AACTAATCAA CCAATGAATT CTATAGGACT     1440

TCTTATTTAT ACTTCTTTAG AATTATATCG ATATAACGGT ACAGAAATTA AGATAATGGA     1500

CATAGAAACT TCAGATCATG ATACTTACAC TCTTACTTCT TATCCAAATC ATAAAGAAGC     1560

ATTATTACTT CTCACAAACC ATTCGTATGA AGAAGTAGAA GAAATAACAA AAATACCTAA     1620

GCATACACTT ATAAAATTGA AAAAACATTA TTTTAAAAAA TAAAAAACAT AATATATAAA     1680

TGACTGATTA ATATCTCTCG AAAAGGTTCT GGTGCAAAAA TAGTGGGATA TGAAAAAAGC     1740

AAAAGATTCC TAACGGAATG GAACATTAGG CTGTTAAATC AAAAAGTTTA TTGATAAAAT     1800

ATATCTGCCT TTGGACAGAC TTCTCCCCTT GGAGAGTTTG TCCTTTTTTG ACCATATGCA     1860

TAGCTTCTAT TCCGGCAATC ATTTTTGTAG CTGTTTGCAA GGATTTTAAT CCAAGCATAT     1920

CCGAATACGC TTTTTGATAA CCGATGTCTT GTTCAATGAT ATTGTTTAAT ATTTTCACAC     1980

GAATTGGCTA CTGTGCGGTA TCCTGTCTCC TTTAT                                2015

(2) INFORMATION FOR SEQ ID NO:31:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

ATGTCAGCTC GCGAAGTACA CATTGAAATA AACAATAAAA CACGTCATAC ATTACAATTA       60

GAGGATAAAA CTAAACTTAG CGGCGGTAGA TGGCGAACAT CACCTACAAA TGTTGCTCGT      120

GATACAATTA AAACATTTGT AGCAGAATCA CATGGTTTTA TGACAGGAGT AGAAGGTATT      180

ATATATTTTA GTGTAAACGG AGACGCAGAA ATTAGTTTAC ATTTTGACAA TCCTTATATA      240

GGTTCTAATA AATGTGATGG TTCTTCTGAT AAACCTGAAT ATGAAGTTAT TACTCAAAGC      300

GGATCAGGAG ATAAATCTCA TGTGACATAT ACTATTCAGA CAGTATCTTT ACGATTATAA      360

(2) INFORMATION FOR SEQ ID NO:32:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:
```

```
Met Ser Ala Arg Glu Val His Ile Glu Ile Asn Asn Lys Thr Arg His
1               5                   10                  15

Thr Leu Gln Leu Glu Asp Lys Thr Lys Leu Ser Gly Gly Arg Trp Arg
            20                  25                  30

Thr Ser Pro Thr Asn Val Ala Arg Asp Thr Ile Lys Thr Phe Val Ala
        35                  40                  45

Glu Ser His Gly Phe Met Thr Gly Val Glu Gly Ile Ile Tyr Phe Ser
    50                  55                  60

Val Asn Gly Asp Ala Glu Ile Ser Leu His Phe Asp Asn Pro Tyr Ile
65                  70                  75                  80

Gly Ser Asn Lys Cys Asp Gly Ser Ser Asp Lys Pro Glu Tyr Glu Val
                85                  90                  95

Ile Thr Gln Ser Gly Ser Gly Asp Lys Ser His Val Thr Tyr Thr Ile
            100                 105                 110

Gln Thr Val Ser Leu Arg Leu
        115
```

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:33:

```
CATGAGATTT ATCTCCTGAT CCGC                                        24
```

(2) INFORMATION FOR SEQ ID NO:34:

(i) SEQUENCE CHARACTERISTICS:
        (A) LENGTH: 2230 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
ACTATGACAA TGATTATGAC TGCTGATGAA TTAGCTTTAT CAATACCAGG ATATTCTAAA    60

CCATCAAATA TAACAGGAGA TAAAAGTAAA CATACATTAT TTACTAATAT AATTGGAGAT   120

ATTCAAATAA AAGATCAAGC AACATTTGGG GTTGTTTTTG ATCCCCCTCT TAATCGTATT   180

TCAGGGGCTG AAGAATCAAG TAAGTTTATT GATGTATATT ATCCTTCTGA AGATAGTAAC   240

CTTAAATATT ATCAATTTAT AAAAGTAGCA ATTGATTTTG ATATTAATGA AGATTTTATT   300

AATTTTAATA ATCATGACAA TATAGGGATA TTTAATTTTG TTACACGAAA TTTTTTATTA   360

AATAATGAAA ATGATTAATA AAAAATTTAA TTTGTATAAT ATGTTTATTT TTTGAAAATT   420

GAATGCATAT ATTAATCGAG TATGTGTAAT AAATTTTAAT TTTATGGAGG TTGATATTTA   480

TGTCAGCACG TGAAGTACAC ATTGATGTAA ATAATAAGAC AGGTCATACA TTACAATTAG   540

AAGATAAAAC AAAACTTGAT GGTGGTAGAT GGCGAACATC ACCTACAAAT GTTGCTAATG   600

ATCAAATTAA AACATTTGTA GCAGAATCAC ATGGTTTTAT GACAGGTACA GAAGGTACTA   660

TATATTTATAG TATAAATGGA GAAGCAGAAA TTAGTTTATA TTTTGACAAT CCTTATTCAG   720

GTTCTAATAA ATATGATGGG CATTCCAATA AAAATCAATA TGAAGTTATT ACCCAAGGAG   780

GATCAGGAAA TCAATCTCAT GTTACGTATA CTATTCAAAC TGTATCTTCA CGATATGGGA   840
```

-continued

```
ATAATTCATA AAAAAATATT TTTTTTTACG AAAATACCAA AAAAATTTTT TTGGTATTTT     900

CTAATATAAT TCATAAATAT TTTAATAATA AAATTATAAG AAAAGGTGAT AAATATTATG     960

TTAGATACTA ATAAAATTTA TGAAATAAGT AATTATGCTA ATGGATTACA TGCAGCAACT    1020

TATTTAAGTT TAGATGATTC AGGTGTTAGT TTAATGAATA AAAATGATGA TGATATTGAT    1080

GACTATAATT TAAGGTGGTT TTTATTTCCT ATTGATGATA ATCAATATAT TATTACAAGC    1140

TACGCAGCGA ATAATTGTAA GGTTTGGAAT GTTAATAATG ATAAAATAAA TGTTTCAACT    1200

TATTCTTCAA CAAACTCGAT ACAGAAATGG CAAATAAAAG CTAATGCTTC TTCGTATGTA    1260

ATACAAAGTA ATAATGGGAA AGTTCTAACA GCAGGAACCG GTCAATCTCT TGGATTAATA    1320

CGTTTAACGG ATGAATCACC AGATAATCCC AATCAACAAT GGAATTTAAC TCCTGTACAA    1380

ACAATTCAAC TCCCACCAAA ACCTACAATA GATACAAAGT TAAAAGATTA CCCCAAATAT    1440

TCACAAACTG GCAATATAGA CAAGGGAACA CCTCCTCAAT TAATGGGATG GACATTAATA    1500

CCTTGTATTA TGGTAAATGA TCCAAATATA GATAAAAACA CTCAAATCAA AACTACTCCA    1560

TATTATATTT TAAAAAAATA TCAATATTGG CAACAAGCAG TAGGAAGTAA TGTAGCTTTA    1620

CGTCCGCATG AAAAAAAATC ATATGCTTAT GAGTGGGGTA CAGAAATAGA TCAAAAAACA    1680

ACTATCATTA ATACATTAGG ATTTCAGATT AATATAGATT CGGGAATGAA ATTTGATATA    1740

CCAGAAGTAG GTGGAGGTAC AGATGAAATA AAAACACAAT TAAACGAAGA ATTAAAAATA    1800

GAATATAGCC GTGAAACCAA AATAATGGAA AAATATCAGG AACAATCAGA GATAGATAAT    1860

CCAACTGATC AATCAATGAA TTCTATAGGA TTCCTCACTA TTACTTCTTT AGAATTATAT    1920

CGATATAATG GTTCGGAAAT TAGTGTAATG AAAATTCAAA CTTCAGATAA TGATACTTAC    1980

AATGTGACCT CTTATCCAGA TCATCAACAA GCTCTATTAC TTCTTACAAA TCATTCATAT    2040

GAAGAAGTAG AAGAAATAAC AAATATTCCC AAAATATCAC TGAAAAAATT AAAAAAATAT    2100

TATTTTTAAA ACATAATTAT ATTTTGATAG CTTTTTAAAA ATAAAGATTG TTCAAAGTAA    2160

AATGAAAGAA AATCTTTTAT GAAACTTTAA TACAATAAAA GAGGAATATT TTCTTATAAG    2220

TACTTCCTTG                                                           2230
```

(2) INFORMATION FOR SEQ ID NO:35:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

```
ATGTCAGCAC GTGAAGTACA CATTGATGTA AATAATAAGA CAGGTCATAC ATTACAATTA      60

GAAGATAAAA CAAAACTTGA TGGTGGTAGA TGGCGAACAT CACCTACAAA TGTTGCTAAT     120

GATCAAATTA AAACATTTGT AGCAGAATCA CATGGTTTTA TGACAGGTAC AGAAGGTACT     180

ATATATTATA GTATAAATGG AGAAGCAGAA ATTAGTTTAT ATTTTGACAA TCCTTATTCA     240

GGTTCTAATA AATATGATGG GCATTCCAAT AAAAATCAAT ATGAAGTTAT TACCCAAGGA     300

GGATCAGGAA ATCAATCTCA TGTTACGTAT ACTATTCAAA CTGTATCTTC ACGATATGGG     360

AATAATTCAT AA                                                         372
```

(2) INFORMATION FOR SEQ ID NO:36:

(i) SEQUENCE CHARACTERISTICS:
            (A) LENGTH: 123 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:36:

```
Met Ser Ala Arg Glu Val His Ile Asp Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Tyr Ser
65                  70                  75                  80

Gly Ser Asn Lys Tyr Asp Gly His Ser Asn Lys Asn Gln Tyr Glu Val
                85                  90                  95

Ile Thr Gln Gly Gly Ser Gly Asn Gln Ser His Val Thr Tyr Thr Ile
            100                 105                 110

Gln Thr Val Ser Ser Arg Tyr Gly Asn Asn Ser
            115                 120
```

(2) INFORMATION FOR SEQ ID NO:37:

(i) SEQUENCE CHARACTERISTICS:
            (A) LENGTH: 1152 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:37:

```
ATGTTAGATA CTAATAAAAT TTATGAAATA AGTAATTATG CTAATGGATT ACATGCAGCA      60

ACTTATTTAA GTTAGATGA TTCAGGTGTT AGTTTAATGA ATAAAAATGA TGATGATATT      120

GATGACTATA ATTTAAGGTG GTTTTTATTT CCTATTGATG ATAATCAATA TATTATTACA      180

AGCTACGCAG CGAATAATTG TAAGGTTTGG AATGTTAATA ATGATAAAAT AAATGTTTCA      240

ACTTATTCTT CAACAAACTC GATACAGAAA TGGCAAATAA AAGCTAATGC TTCTTCGTAT      300

GTAATACAAA GTAATAATGG GAAAGTTCTA ACAGCAGGAA CCGGTCAATC TCTTGGATTA      360

ATACGTTTAA CGGATGAATC ACCAGATAAT CCCAATCAAC AATGGAATTT AACTCCTGTA      420

CAAACAATTC AACTCCCACC AAAACCTACA ATAGATACAA AGTTAAAAGA TTACCCCAAA      480

TATTCACAAA CTGGCAATAT AGACAAGGGA ACACCTCCTC AATTAATGGG ATGGACATTA      540

ATACCTTGTA TTATGGTAAA TGATCCAAAT ATAGATAAAA ACACTCAAAT CAAAACTACT      600

CCATATTATA TTTTAAAAAA ATATCAATAT TGGCAACAAG CAGTAGGAAG TAATGTAGCT      660

TTACGTCCGC ATGAAAAAAA ATCATATGCT TATGAGTGGG GTACAGAAAT AGATCAAAAA      720

ACAACTATCA TTAATACATT AGGATTTCAG ATTAATATAG ATTCGGGAAT GAAATTTGAT      780

ATACCAGAAG TAGGTGGAGG TACAGATGAA ATAAAAACAC AATTAAACGA AGAATTAAAA      840

ATAGAATATA GCCGTGAAAC CAAAATAATG GAAAATATC AGGAACAATC AGAGATAGAT      900

AATCCAACTG ATCAATCAAT GAATTCTATA GGATTCCTCA CTATTACTTC TTTAGAATTA      960
```

```
TATCGATATA ATGGTTCGGA AATTAGTGTA ATGAAAATTC AAACTTCAGA TAATGATACT    1020

TACAATGTGA CCTCTTATCC AGATCATCAA CAAGCTCTAT TACTTCTTAC AAATCATTCA    1080

TATGAAGAAG TAGAAGAAAT AACAAATATT CCCAAAATAT CACTGAAAAA ATTAAAAAAA    1140

TATTATTTTT AA                                                        1152
```

(2) INFORMATION FOR SEQ ID NO:38:

(i) SEQUENCE CHARACTERISTICS:
        (A) LENGTH: 383 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

```
Met Leu Asp Thr Asn Lys Ile Tyr Glu Ile Ser Asn Tyr Ala Asn Gly
1               5                  10                  15

Leu His Ala Ala Thr Tyr Leu Ser Leu Asp Asp Ser Gly Val Ser Leu
            20                  25                  30

Met Asn Lys Asn Asp Asp Ile Asp Asp Tyr Asn Leu Arg Trp Phe
        35                  40                  45

Leu Phe Pro Ile Asp Asp Asn Gln Tyr Ile Ile Thr Ser Tyr Ala Ala
50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
            85                  90                  95

Ala Ser Ser Tyr Val Ile Gln Ser Asn Asn Gly Lys Val Leu Thr Ala
            100                 105                 110

Gly Thr Gly Gln Ser Leu Gly Leu Ile Arg Leu Thr Asp Glu Ser Pro
        115                 120                 125

Asp Asn Pro Asn Gln Gln Trp Asn Leu Thr Pro Val Gln Thr Ile Gln
130                 135                 140

Leu Pro Pro Lys Pro Thr Ile Asp Thr Lys Leu Lys Asp Tyr Pro Lys
145                 150                 155                 160

Tyr Ser Gln Thr Gly Asn Ile Asp Lys Gly Thr Pro Pro Gln Leu Met
            165                 170                 175

Gly Trp Thr Leu Ile Pro Cys Ile Met Val Asn Asp Pro Asn Ile Asp
        180                 185                 190

Lys Asn Thr Gln Ile Lys Thr Thr Pro Tyr Tyr Ile Leu Lys Lys Tyr
195                 200                 205

Gln Tyr Trp Gln Gln Ala Val Gly Ser Asn Val Ala Leu Arg Pro His
210                 215                 220

Glu Lys Lys Ser Tyr Ala Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
            245                 250                 255

Met Lys Phe Asp Ile Pro Glu Val Gly Gly Thr Asp Glu Ile Lys
        260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
290                 295                 300

Gln Ser Met Asn Ser Ile Gly Phe Leu Thr Ile Thr Ser Leu Glu Leu
```

```
305                 310                 315                 320
Tyr Arg Tyr Asn Gly Ser Glu Ile Ser Val Met Lys Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ile Ser Leu Lys Lys Leu Lys Lys Tyr Tyr Phe
    370                 375                 380
```

(2) INFORMATION FOR SEQ ID NO:39:

(i) SEQUENCE CHARACTERISTICS:
        (A) LENGTH: 2132 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
GTATTTCAGG GGGTGAAGAT TCAAGTAAGT TTATTGATGT ATATTATCCT TTTGAAGATA      60

GTAATTTTAA ATATTATCAA TTTATAAAAG TAGCAATTGA TTTTGATATT AATGAAGATT     120

TTATTAATTT TAATAATCAT GACAATATAG GGATATTTAA TTTTGTTACA CGAAATTTTT     180

TATTAAATAA TGAAAATGAT GAATAAAAAA TTTAATTTGT TTATTATGTT TATTTTTTGA     240

AAATTGAATG CATATATTAA TCGAGTATGT ATAATAAATT TTAATTTTAT GGAGGTTGAT     300

ATTTATGTCA GCACGTGAAG TACACATTGA TGTAAATAAT AAGACAGGTC ATACATTACA     360

ATTAGAAGAT AAAACAAAAC TTGATGGTGG TAGATGGCGA ACATCACCTA CAAATGTTGC     420

TAATGATCAA ATTAAAACAT TTGTAGCAGA ATCAAATGGT TTTATGACAG GTACAGAAGG     480

TACTATATAT TATAGTATAA ATGGAGAAGC AGAAATTAGT TTATATTTTG ACAATCCTTT     540

TGCAGGTTCT AATAAATATG ATGGACATTC CAATAAATCT CAATATGAAA TTATTACCCA     600

AGGAGGATCA GGAAATCAAT CTCATGTTAC GTATACTATT CAAACCACAT CCTCACGATA     660

TGGGCATAAA TCATAACAAA TAATTTTTTA CGAAAATACC AAAAAATAAA TATTTTTTGG     720

TATTTTCTAA TATAAATTAC AAATATATTA ATAATAAAAT TATAAGAAAA GGTGATAAAG     780

ATTATGTTAG ATACTAATAA AGTTTATGAA ATAAGCAATC ATGCTAATGG ACTATATGCA     840

GCAACTTATT TAAGTTTAGA TGATTCAGGT GTTAGTTTAA TGAATAAAAA TGATGATGAT     900

ATTGATGATT ATAACTTAAA ATGGTTTTTA TTTCCTATTG ATGATGATCA ATATATTATT     960

ACAAGCTATG CAGCAAATAA TTGTAAAGTT TGGAATGTTA ATAATGATAA AATAAATGTT    1020

TCGACTTATT CTTCAACAAA TTCAATACAA AAATGGCAAA TAAAAGCTAA TGGTTCTTCA    1080

TATGTAATAC AAAGTGATAA TGGAAAAGTC TTAACAGCAG GAACCGGTCA AGCTCTTGGA    1140

TTGATACGTT TAACTGATGA ATCCTCAAAT AATCCCAATC AACAATGGAA TTTAACTTCT    1200

GTACAAACAA TTCAACTTCC ACAAAAACCT ATAATAGATA CAAAATTAAA AGATTATCCC    1260

AAATATTCAC CAACTGGAAA TATAGATAAT GGAACATCTC CTCAATTAAT GGGATGGACA    1320

TTAGTACCTT GTATTATGGT AAATGATCCA AATATAGATA AAAATACTCA AATTAAAACT    1380

ACTCCATATT ATATTTTAAA AAAATATCAA TATTGGCAAC GAGCAGTAGG AAGTAATGTA    1440

GCTTTACGTC CACATGAAAA AAAATCATAT ACTTATGAAT GGGGCACAGA AATAGATCAA    1500

AAAACAACAA TTATAAATAC ATTAGGATTT CAAATCAATA TAGATTCAGG AATGAAATTT    1560
```

```
GATATACCAG AAGTAGGTGG AGGTACAGAT GAAATAAAAA CACAACTAAA TGAAGAATTA    1620

AAAATAGAAT ATAGTCATGA AACTAAAATA ATGGAAAAAT ATCAAGAACA ATCTGAAATA    1680

GATAATCCAA CTGATCAATC AATGAATTCT ATAGGATTTC TTACTATTAC TTCCTTAGAA    1740

TTATATAGAT ATAATGGCTC AGAAATTCGT ATAATGCAAA TTCAAACCTC AGATAATGAT    1800

ACTTATAATG TTACTTCTTA TCCAAATCAT CAACAAGCTT TATTACTTCT TACAAATCAT    1860

TCATATGAAG AAGTAGAAGA AATAACAAAT ATTCCTAAAA GTACACTAAA AAAATTAAAA    1920

AAATATTATT TTTAAATATT GAAATTAGAA ATTATCTAAA ACAAAACGAA AGATAATTTA    1980

ATCTTTAATT ATTTGTAAGA TAATCGTATT TTATTTGTAT TAATTTTTAT ACAATATAAA    2040

GTAATATCTG TACGTGAAAT TGGTTTCGCT TCAATATCTA ATCTCATCTC ATGTATTACA    2100

TGCGTAATAC CTTCTTGTTC TGCTTCTACA AG                                 2132

(2) INFORMATION FOR SEQ ID NO:40:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

ATGTCAGCAC GTGAAGTACA CATTGATGTA AATAATAAGA CAGGTCATAC ATTACAATTA      60

GAAGATAAAA CAAAACTTGA TGGTGGTAGA TGGCGAACAT CACCTACAAA TGTTGCTAAT     120

GATCAAATTA AACATTTGT AGCAGAATCA AATGGTTTTA TGACAGGTAC AGAAGGTACT     180

ATATATTATA GTATAAATGG AGAAGCAGAA ATTAGTTTAT ATTTTGACAA TCCTTTTGCA     240

GGTTCTAATA AATATGATGG ACATTCCAAT AAATCTCAAT ATGAAATTAT TACCCAAGGA     300

GGATCAGGAA ATCAATCTCA TGTTACGTAT ACTATTCAAA CCACATCCTC ACGATATGGG     360

CATAAATCAT AA                                                          372

(2) INFORMATION FOR SEQ ID NO:41:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

Met Ser Ala Arg Glu Val His Ile Asp Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser Asn Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Phe Ala
65                  70                  75                  80

Gly Ser Asn Lys Tyr Asp Gly His Ser Asn Lys Ser Gln Tyr Glu Ile
                85                  90                  95

Ile Thr Gln Gly Gly Ser Gly Asn Gln Ser His Val Thr Tyr Thr Ile
```

```
              100                 105                 110
Gln Thr Thr Ser Ser Arg Tyr Gly His Lys Ser
        115                 120

(2) INFORMATION FOR SEQ ID NO:42:

(i) SEQUENCE CHARACTERISTICS:
        (A) LENGTH: 1152 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

ATGTTAGATA CTAATAAAGT TTATGAAATA AGCAATCATG CTAATGGACT ATATGCAGCA      60

ACTTATTTAA GTTTAGATGA TTCAGGTGTT AGTTTAATGA ATAAAAATGA TGATGATATT     120

GATGATTATA ACTTAAAATG GTTTTTATTT CCTATTGATG ATGATCAATA TATTATTACA     180

AGCTATGCAG CAAATAATTG TAAAGTTTGG AATGTTAATA ATGATAAAAT AAATGTTTCG     240

ACTTATTCTT CAACAAATTC AATACAAAAA TGGCAAATAA AAGCTAATGG TTCTTCATAT     300

GTAATACAAA GTGATAATGG AAAAGTCTTA ACAGCAGGAA CCGGTCAAGC TCTTGGATTG     360

ATACGTTTAA CTGATGAATC CTCAAATAAT CCCAATCAAC AATGGAATTT AACTTCTGTA     420

CAAACAATTC AACTTCCACA AAAACCTATA ATAGATACAA AATTAAAAGA TTATCCCAAA     480

TATTCACCAA CTGGAAATAT AGATAATGGA ACATCTCCTC AATTAATGGG ATGGACATTA     540

GTACCTTGTA TTATGGTAAA TGATCCAAAT ATAGATAAAA ATACTCAAAT TAAAACTACT     600

CCATATTATA TTTTAAAAAA ATATCAATAT TGGCAACGAG CAGTAGGAAG TAATGTAGCT     660

TTACGTCCAC ATGAAAAAAA ATCATATACT TATGAATGGG GCACAGAAAT AGATCAAAAA     720

ACAACAATTA TAAATACATT AGGATTTCAA ATCAATATAG ATTCAGGAAT GAAATTTGAT     780

ATACCAGAAG TAGGTGGAGG TACAGATGAA ATAAAAACAC AACTAAATGA AGAATTAAAA     840

ATAGAATATA GTCATGAAAC TAAAATAATG GAAAAATATC AAGAACAATC TGAAATAGAT     900

AATCCAACTG ATCAATCAAT GAATTCTATA GGATTTCTTA CTATTACTTC CTTAGAATTA     960

TATAGATATA ATGGCTCAGA AATTCGTATA ATGCAAATTC AAACCTCAGA TAATGATACT    1020

TATAATGTTA CTTCTTATCC AAATCATCAA CAAGCTTTAT TACTTCTTAC AAATCATTCA    1080

TATGAAGAAG TAGAAGAAAT AACAAATATT CCTAAAAGTA CACTAAAAAA ATTAAAAAAA    1140

TATTATTTTT AA                                                        1152

(2) INFORMATION FOR SEQ ID NO:43:

(i) SEQUENCE CHARACTERISTICS:
        (A) LENGTH: 383 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

Met Leu Asp Thr Asn Lys Val Tyr Glu Ile Ser Asn His Ala Asn Gly
1               5                  10                  15

Leu Tyr Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Lys Trp Phe
        35                  40                  45
```

```
Leu Phe Pro Ile Asp Asp Gln Tyr Ile Ile Thr Ser Tyr Ala Ala
     50                  55                  60

Asn Asn Cys Lys Val Trp Asn Val Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Gly Ser Ser Tyr Val Ile Gln Ser Asp Asn Gly Lys Val Leu Thr Ala
                100                 105                 110

Gly Thr Gly Gln Ala Leu Gly Leu Ile Arg Leu Thr Asp Glu Ser Ser
            115                 120                 125

Asn Asn Pro Asn Gln Gln Trp Asn Leu Thr Ser Val Gln Thr Ile Gln
130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
            195                 200                 205

Gln Tyr Trp Gln Arg Ala Val Gly Ser Asn Val Ala Leu Arg Pro His
            210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Thr Asp Glu Ile Lys
            260                 265                 270

Thr Gln Leu Asn Glu Glu Leu Lys Ile Glu Tyr Ser His Glu Thr Lys
            275                 280                 285

Ile Met Glu Lys Tyr Gln Glu Gln Ser Glu Ile Asp Asn Pro Thr Asp
290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Ser Tyr Pro Asn His Gln Gln Ala
            340                 345                 350

Leu Leu Leu Leu Thr Asn His Ser Tyr Glu Glu Val Glu Glu Ile Thr
            355                 360                 365

Asn Ile Pro Lys Ser Thr Leu Lys Lys Leu Lys Lys Tyr Tyr Phe
370                 375                 380

(2) INFORMATION FOR SEQ ID NO:44:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

ATGTCCGCCC GCGAGGTGCA CATCGAGATC AACAACAAGA CCCGCCACAC CCTCCAGCTC     60
```

-continued

```
GAGGACAAGA CCAAGCTCTC CGGCGGCAGG TGGCGCACCT CCCCGACCAA CGTGGCCCGC      120

GACACCATCA AGACGTTCGT GGCGGAGTCC CACGGCTTCA TGACCGGCGT CGAGGGCATC      180

ATCTACTTCT CCGTGAACGG CGACGCCGAG ATCTCCCTCC ACTTCGACAA CCCGTACATC      240

GGCTCCAACA AGTGCGACGG CTCCTCCGAC AAGCCCGAGT ACGAGGTGAT CACCCAGTCC      300

GGCTCCGGCG ACAAGTCCCA CGTGACCTAC ACCATCCAGA CCGTGTCCCT CCGCCTCTGA      360
```

(2) INFORMATION FOR SEQ ID NO:45:

(i) SEQUENCE CHARACTERISTICS:
        (A) LENGTH: 1158 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

```
ATGCTCGACA CCAACAAGGT GTACGAGATC TCCAACCTCG CCAACGGCCT CTACACCTCC       60

ACCTACCTCT CCCTCGACGA CTCCGGCGTG TCCCTCATGT CCAAGAAGGA CGAGGACATC      120

GACGACTACA ACCTCAAGTG GTTCCTCTTC CCGATCGACA ACAACCAGTA CATCATCACC      180

TCCTACGGCG CCAACAACTG CAAGGTGTGG AACGTGAAGA ACGACAAGAT CAACGTGTCC      240

ACCTACTCCT CCACCAACTC CGTGCAGAAG TGGCAGATCA AGGCCAAGGA CTCCTCCTAC      300

ATCATCCAGT CCGACAACGG CAAGGTGCTC ACCGCGGGCG TGGGCCAGTC CCTCGGCATC      360

GTGCGCCTCA CCGACGAGTT CCCGGAGAAC TCCAACCAGC AATGGAACCT CACCCCGGTG      420

CAGACCATCC AGCTCCCGCA GAAGCCGAAG ATCGACGAGA AGCTCAAGGA CCACCCGGAG      480

TACTCCGAGA CCGGCAACAT CAACCCGAAG ACCACCCCGC AGCTCATGGG CTGGACCCTC      540

GTGCCGTGCA TCATGGTGAA CGACTCCAAG ATCGACAAGA ACACCCAGAT CAAGACCACC      600

CCGTACTACA TCTTCAAGAA ATACAAGTAC TGGAACCTCG CCAAGGGCTC CAACGTGTCC      660

CTCCTCCCGC ACCAGAAGCG CAGCTACGAC TACGAGTGGG GCACCGAGAA GAACCAGAAG      720

ACCACCATCA TCAACACCGT GGGCCTGCAG ATCAACATCG ACTCGGGGAT GAAGTTCGAG      780

GTGCCGGAGG TGGGCGGCGG CACCGAGGAC ATCAAGACCC AGCTCACCGA GGAGCTGAAG      840

GTGGAGTACT CCACCGAGAC CAAGATCATG ACCAAGTACC AGGAGCACTC CGAGATCGAC      900

AACCCGACCA ACCAGCCGAT GAACTCCATC GGCCTCCTCA TCTACACCTC CCTCGAGCTG      960

TACCGCTACA ACGGCACCGA GATCAAGATC ATGGACATCG AGACCTCCGA CCACGACACC     1020

TACACCCTCA CCTCCTACCC GAACCACAAG GAGGCGCTGC TGCTGCTGAC CAACCACTCC     1080

TACGAGGAGG TGGAGGAGAT CACCAAGATC CCGAAGCACA CCCTCATCAA GCTCAAGAAG     1140

CACTACTTCA AGAAGTGA                                                    1158
```

PESTICIDAL TOXINS

CROSS-REFERENCE TO A RELATED APPLICATION

This application is a continuation-in-part of application Ser. No. 08/633,993, filed Apr. 19, 1996, pending.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] TIBTECH 6:S4–S7). Thus, isolated B.t. endotoxin genes are becoming commercially valuable.

Until the last ten years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely *israelensis* and *tenebrionis* (a.k.a. B.t. M-7, a.k.a. B.t. san diego), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Baccillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a B.t. crystal protein gene in *Escherichia coli* has been described in the published literature (Schnepf, H. E., H. R. Whiteley [1981] *Proc. Natl. Acad. Sci USA* 78:2893–2897). U.S. Pat. No. 4,448,885 and U.S. Pat. No. 4,467,036 both disclose the expression of B.t. crystal protein in *E. coli*. U.S. Pat. Nos. 4,797,276 and 4,853,331 disclose *B. thuringiensis* strain *tenebrionis* (a.k.a. M-7, a.k.a. B.t. san diego) which can be used to control coleopteran pests in various environments. U.S. Pat. No. 4,918,006 discloses B.t. toxins having activity against Dipterans. U.S. Pat. No. 4,849,217 discloses B.t. isolates which have activity against the alfalfa weevil. U.S. Pat. No. 5,208,017 discloses coleopteran-active *Bacillus thuringiensis* isolates. U.S. Pat. No. 5,151,363 and U.S. Pat. No. 4,948,734 disclose certain isolates of B.t. which have activity against nematodes. As a result of extensive research and investment of resources, other patents have issued for new B.t. isolates and new uses of B.t. isolates. However, the discovery of new B.t. isolates and new uses of known B.t. isolates remains an empirical, unpredictable art.

Coleopterans are an important group of agricultural pests which cause a very large amount of damage each year. Examples of coleopteran pests include alfalfa weevils and corn rootworm.

The alfalfa weevil, *Hypera postica*, and the closely related Egyptian alfalfa weevil, *Hypera brunneipennis*, are the most important insect pests of alfalfa grown in the United States, with 2.9 million acres infested in 1984. An annual sum of 20 million dollars is spent to control these pests. The Egyptian alfalfa weevil is the predominant species in the southwestern U.S., where it undergoes aestivation (i.e., hibernation) during the hot summer months. In all other respects, it is identical to the alfalfa weevil, which predominates throughout the rest of the U.S.

The larval stage is the most damaging in the weevil life cycle. By feeding at the alfalfa plant's growing tips, the larvae cause skeletonization of leaves, stunting, reduced plant growth, and, ultimately, reductions in yield. Severe infestations can ruin an entire cutting of hay. The adults, also foliar feeders, cause additional, but less significant, damage.

Approximately 9.3 million acres of U.S. corn are infested with corn rootworm species complex each year. The corn rootworm species complex includes the northern corn rootworm, *Diabrotica barberi*, the southern corn rootworm, *D. undecimpunctata howardi*, and the western corn rootworm, *D. virgifera virgifera*. The soil-dwelling larvae of these Diabrotica species feed on the root of the corn plant, causing lodging. Lodging eventually reduces corn yield and often results in death of the plant. By feeding on cornsilks, the adult beetles reduce pollination and, therefore, detrimentally effect the yield of corn per plant. In addition, adults and larvae of the genus Diabrotica attack cucurbit crops (cucumbers, melons, squash, etc.) and many vegetable and field crops in commercial production as well as those being grown in home gardens.

Control of corn rootworm has been partially addressed by cultivation methods, such as crop rotation and the application of high nitrogen levels to stimulate the growth of an adventitious root system. However, chemical insecticides are relied upon most heavily to guarantee the desired level of control. Insecticides are either banded onto or incorporated into the soil. The major problem associated with the use of chemical insecticides is the development of resistance among the treated insect populations.

BRIEF SUMMARY OF THE INVENTION

The subject invention concerns novel materials and methods for controlling non-mammalian pests. In a preferred embodiment, the subject invention provides materials sand methods for the control of coleopteran pests. In specific embodiments, the materials and methods described herein are used to control alfalfa weevil and/or corn rootworm.

The subject invention advantageously provides two new classes of polynucleotide sequences which encode corresponding novel classes of pesticidal proteins. One novel class of polynucleotide sequences as described herein encodes toxins which have a full-length molecular weight of approximately 40–50 kDa. In a specific embodiment, these toxins have a molecular weight of about 43–47 kDa. A second class of polynucleotides, which encodes pesticidal proteins of about 10–15 kDa, is also provided according to the subject invention. In a specific embodiment, these toxins have a molecular weight of about 13–14 kDa. The subject invention concerns polynucleotides which encode the 40–50 kDa and 10–15 kDa toxins, polynucleotides which encode pesticidal fragments of the full length toxins, and polynucleotide sequences which encode longer forms of these toxins which include, for example, a protoxin region. In a preferred embodiment, these toxins, including the fragments, are active against coleopteran pests.

Specific B.t. toxins useful according to the invention include toxins which can be obtained from the B.t. isolates designated as PS80JJ1, PS149B1, and PS167H2. Of these, PS149B1 and PS167H2 are novel isolates. The subject invention also includes the use of variants of the exemplified B.t. isolates and toxins which have substantially the same coleopteran-active properties as the specifically exemplified B.t. isolates and toxins. Such variant isolates would include, for example, mutants. Procedures for making mutants are well known in the microbiological art. Ultraviolet light and chemical mutagens such as nitrosoguanidine are used extensively toward this end.

In one embodiment of the subject invention, the polynucleotide sequences of the subject invention are used to encode toxins of approximately 43–47 kDa. These toxins are then used to control coleopteran pests. In a particularly preferred embodiment, the coleopteran pests are corn rootworms. The genes which encode the 43–47 kDa toxins can be obtained from, for example, PS80JJ1, PS149B1, or PS167H2. In a second embodiment, toxins of approximately 13–14 kDa are used to control coleopteran pests. The approximately 13–14 kDa toxin, as well as the genes which encode these toxins, can also be obtained from PS80JJ1, PS149B1, or PS167H2. In a particularly preferred embodiment, the activity of the 43–47 kDa toxins can be augmented and/or facilitated by further contacting the target pests with an approximately 13–14 kDa toxin.

In a preferred embodiment, the subject invention concerns plants cells transformed with at least one polynucleotide sequence of the subject invention such that the transformed plant cells express pesticidal toxins in tissues consumed by the target pests.

Alternatively, the B.t. isolates of the subject invention, or recombinant microbes expressing the toxins described herein, can be used to control pests. In this regard, the invention includes the treatment of substantially intact B.t. cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

BRIEF DESCRIPTION OF THE DRAWINGS

FIG. 1 shows three specific 43–47 kDa pesticidal toxins of the subject invention as well as a consensus sequence for these pesticidal toxins.

BRIEF DESCRIPTION OF THE SEQUENCES

Figure 2:
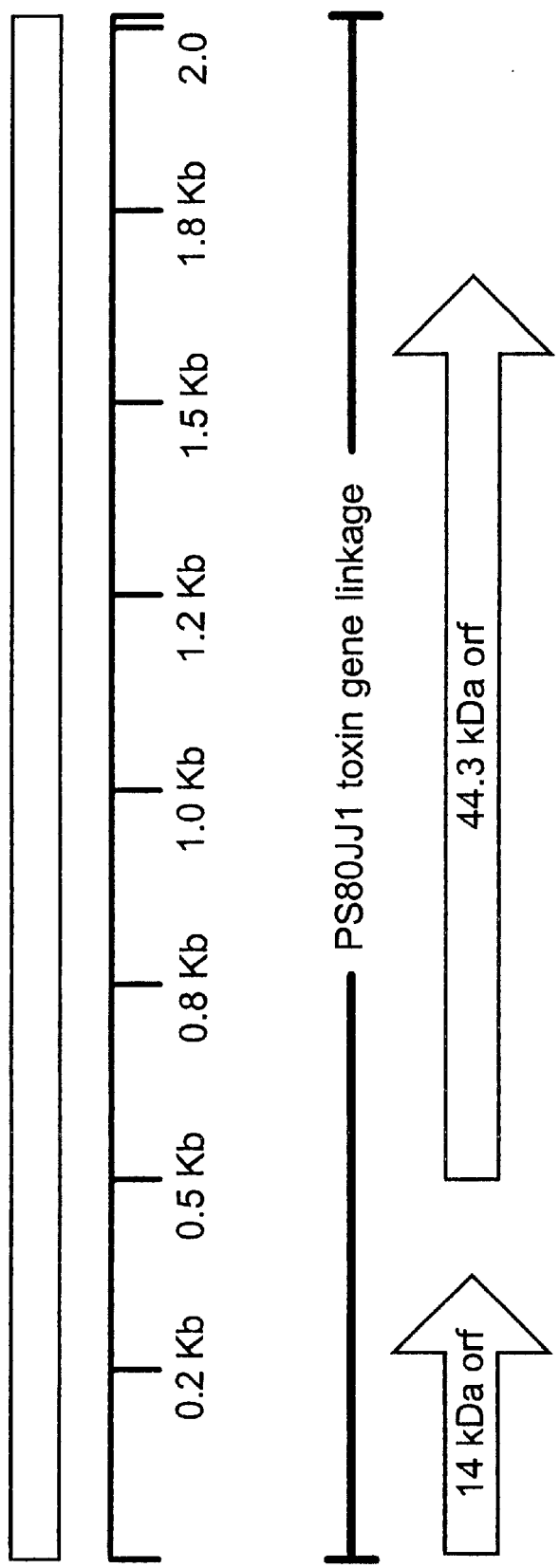
FIG. 2 shows the relationship of the 14 and 45 kDa sequences of PS80JJ1 (SEQ ID NOS. 31 and 10).

SEQ ID NO. 1 is a 5-amino acid N-terminal sequence of the approximately 45 kDa toxin of 80JJ1.

SEQ ID NO. 2 is a 25-amino acid N-terminal sequence of the approximately 45 kDa toxin of 80JJ1.

SEQ ID NO. 3 is a 24-amino acid N-terminal sequence of the approximately 14 kDa toxin of 80JJ1.

SEQ ID NO. 4 is the N-terminal sequence of the approximately 47 kDa toxin from 149B1.

SEQ ID NO. 5 is a 50-amino acid N-terminal amino acid sequence for the purified approximately 14 kDa protein from PS149B1.

SEQ ID NO. 6 is the N-terminal sequence of the approximately 47 kDa toxin from 167H2.

SEQ ID NO. 7 is a 25-amino acid N-terminal sequence for the purified approximately 14 kDa protein from PS167H2.

SEQ ID NO. 8 is an oligonucleotide probe for the gene encoding the PS80JJ1 44.3 kDa toxin and is a forward primer for PS149B1 and PS167H2 used according to the subject invention.

SEQ ID NO. 9 is a reverse primer for PS149B1 and PS167H2 used according to the subject invention.

SEQ ID NO. 10 is the nucleotide sequence of the gene encoding the approximately 45 kDa PS80JJ1 toxin.

SEQ ID NO. 11 is the amino acid sequence for the approximately 45 kDa PS80JJ1 toxin.

SEQ ID NO. 12 is the partial nucleotide sequence of the gene encoding the approximately 44 kDa PS149B1 toxin.

SEQ ID NO. 13 is the partial amino acid sequence for the approximately 44 kDa PS149B1 toxin.

SEQ ID NO. 14 is the partial nucleotide sequence of the gene encoding the approximately 44 kDa PS167H2 toxin.

SEQ ID NO. 15 is the partial amino acid sequence for the approximately 44 kDa PS167H2 toxin.

SEQ ID NO. 16 is a peptide sequence used in primer design according to the subject invention.

SEQ ID NO. 17 is a peptide sequence used in primer design according to the subject invention.

SEQ ID NO. 18 is a peptide sequence used in primer design according to the subject invention.

SEQ ID NO. 19 is a peptide sequence used in primer design according to the subject invention.

SEQ ID NO. 20 is a nucleotide sequence corresponding to the peptide of SEQ ID NO. 16.

SEQ ID NO. 21 is a nucleotide sequence corresponding to the peptide of SEQ ID NO. 17.

SEQ ID NO. 22 is a nucleotide sequence corresponding to the peptide of SEQ ID NO. 18.

SEQ ID NO. 23 is a nucleotide sequence corresponding to the peptide of SEQ ID NO. 19.

SEQ ID NO. 24 is a reverse primer based on the reverse complement of SEQ ID NO. 22.

SEQ ID NO. 25 is a reverse primer based on the reverse complement of SEQ ID NO. 23.

SEQ ID NO. 26 is a forward primer based on the PS80JJ1 44.3 kDa toxin.

SEQ ID NO. 27 is a reverse primer based on the PS80JJ1 44.3 kDa toxin.

SEQ ID NO. 28 is a generic sequence representing a new class of toxins according to the subject invention.

SEQ ID NO. 19 is an oligonucleotide probe used according to the subject invention.

SEQ ID NO. 30 is the nucleotide sequence of the entire genetic locus containing open reading frames of both the 14 and 45 kDa PS80JJ1 toxins and the flanking nucleotide sequences.

SEQ ID NO. 31 is the nucleotide sequence of the PS80JJ1 14 kDa toxin open reading frame.

SEQ ID NO. 32 is the deduced amino acid sequence of the 14 kDa toxin of PS80JJ1.

SEQ ID NO. 33 is a reverse oligonucleotide primer used according to the subject invention.

SEQ ID NO. 34 is the nucleotide sequence of the entire genetic locus containing open reading frames of both the 14 and 44 kDa PS167H2 toxins and the flanking nucleotide sequences.

SEQ ID NO. 35 is the nucleotide sequence of the gene encoding the approximately 14 kDa PS167H2 toxin.

SEQ ID NO. 36 is the amino acid sequence for the approximately 14 kDa PS167H2 toxin.

SEQ ID NO. 37 is the nucleotide sequence of the gene encoding the approximately 44 kDa PS167H2 toxin.

SEQ ID NO. 38 is the amino acid sequence for the approximately 44 kDa PS167H2 toxin.

SEQ ID NO. 39 is the nucleotide sequence of the entire genetic locus containing open reading frames of both the 14 and 44 kDa PS149B1 toxins and the flanking nucleotide sequences.

SEQ ID NO. 40 is the nucleotide sequence of the gene encoding the approximately 14 kDa PS149B1 toxin.

SEQ ID NO. 41 is the amino acid sequence for the approximately 14 kDa PS149B1 toxin.

SEQ ID NO. 42 is the nucleotide sequence of the gene encoding the approximately 44 kDa PS149B1 toxin.

SEQ ID NO. 43 is the amino acid sequence for the approximately 44 kDa PS149B1 toxin.

SEQ ID NO. 44 is a maize-optimized gene sequence encoding the approximately 14 kDa toxin of 80JJ1.

SEQ ID NO. 45 is a maize-optimized gene sequence encoding the approximately 44 kDa toxin of 80JJ1.

DETAILED DISCLOSURE OF THE INVENTION

The subject invention concerns two new classes of polynucleotide sequences which encode novel pesticidal toxins. In one embodiment, the toxins have a full-length molecular weight of approximately 40–50 kDa. In specific embodiments exemplified herein, these toxins have a molecular weight of about 43–47 kDa. In a second embodiment, the pesticidal toxins have a molecular weight of approximately 10–15 kDa. In specific embodiments exemplified herein, these toxins have a molecular weight of about 13–14 kDa. Certain specific toxins are exemplified herein. For toxins having a known amino acid sequence, the molecular weight is also known. Those skilled in the art will recognize that the apparent molecular weight of a protein as determined by gel electrophoresis will sometimes differ from the true molecular weight. Therefore, reference herein to, for example, a 45 kDa protein or a 14 kDa protein is understood to refer to proteins of approximately that size even if the true molecular weight is somewhat different.

The subject invention concerns not only the polynucleotide sequences which encode these classes of toxins, but also the use of these polynucleotide sequences to produce recombinant hosts which express the toxins. In a further aspect, the subject invention concerns the combined use of an approximately 40–50 kDa toxin of the subject invention together with an approximately 10–15 kDa toxin of the subject invention to achieve highly effective control of pests, including coleopterans such as corn rootworm.

A further aspect of the subject invention concerns two novel isolates and the toxins and genes obtainable from these isolates. The novel B.t. isolates of the subject invention have been designated PS149B1 and PS167H2.

The new classes of toxins and polynucleotide sequences provided here are defined according to several parameters. One critical characteristic of the toxins described herein is pesticidal activity. In a specific embodiment, these toxins have activity against coleopteran pests. The toxins and genes of the subject invention can be further defined by their amino acid and nucleotide sequences. The sequences of the molecules within each novel class can be defined herein in terms of homology to certain exemplified sequences as well as in terms of the ability to hybridize with, or be amplified by, certain exemplified probes and primers. The classes of toxins provided herein can also be identified based on their immunoreactivity with certain antibodies and based upon their adherence to a generic formula.

The sequence of three approximately 45 kDa toxins of the subject invention are provided as SEQ ID NOS. 11, 43, and 38. In a preferred embodiment of the subject invention, the toxins in this new class have a sequence which conforms to the generic sequence presented as SEQ ID NO. 28. In a specific embodiment, the toxins of this class will conform to the consensus sequence shown in FIG. 1.

In a preferred embodiment, the toxins of the subject invention have at least one of the following characteristics:

(a) said toxin is encoded by a nucleotide sequence which hybridizes under stringent conditions with a nucleotide sequence selected from the group consisting of: DNA which encodes SEQ ID NO. 2, DNA which encodes SEQ ID NO. 4, DNA which encodes SEQ ID NO. 6, SEQ ID NO. 8, SEQ ID NO. 10, DNA which encodes SEQ ID NO. 11, SEQ ID NO. 12, DNA which encodes SEQ ID NO. 13, SEQ ID NO. 14, DNA which encodes SEQ ID NO. 15, DNA which encodes SEQ ID NO. 16, DNA which encodes SEQ ID NO. 17, DNA which encodes SEQ ID NO. 18, DNA which encodes SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, DNA which encodes a pesticidal portion of SEQ ID NO. 28, SEQ ID NO. 37, DNA which encodes SEQ ID NO. 38, SEQ ID NO. 42, and DNA which encodes SEQ ID NO. 43;

(b) said toxin immunoreacts with an antibody to an approximately 40–50 kDa pesticidal toxin, or a fragment thereof, from a *Bacillus thuringiensis* isolate selected from the group consisting of PS80JJ1 having the identifying characteristics of NRRL B-18679, PS149B1 having the identifying characteristics of NRRL B-21553, and PS167H2 having the identifying characteristics of NRRL B-21554;

(c) said toxin is encoded by a nucleotide sequence wherein a portion of said nucleotide sequence can be amplified by PCR using a primer pair selected from the group consisting of SEQ ID NOS. 20 and 24 to produce a fragment of about 495 bp, SEQ ID NOS. 20 and 25 to produce a fragment of about 594 bp, SEQ ID NOS. 21 and 24 to produce a fragment of about 471 bp, and SEQ ID NOS. 21 and 25 to produce a fragment of about 580 bp;

(d) said toxin comprises a pesticidal portion of the amino acid sequence shown in SEQ ID NO. 28;

(e) said toxin comprises an amino acid sequence which has at least about 60% homology with a pesticidal portion of an amino acid sequence selected from the group consisting of SEQ ID NO. 11, SEQ ID NO. 13, SEQ ID NO. 15, SEQ ID NO. 38, and SEQ ID NO. 43;

(f) said toxin is encoded by a nucleotide sequence which hybridizes under stringent conditions with a nucleotide sequence selected from the group consisting of DNA which encodes SEQ ID NO. 3, DNA which encodes SEQ ID NO. 5, DNA which encodes SEQ ID NO. 7, DNA which encodes SEQ ID NO. 32, DNA which encodes SEQ ID NO. 36, and DNA which encodes SEQ ID NO. 41;

(g) said toxin immunoreacts with an antibody to an approximately 10–15 kDa pesticidal toxin, or a fragment thereof, from a *Bacillus thuringiensis* isolate selected from the group consisting of PS80JJ1 having the identifying characteristics of NRRL B-18679, PS149B1 having the identifying characteristics of NRRL B-21553, and PS167H2 having the identifying characteristics of NRRL B-21554;

(h) said toxin is encoded by a nucleotide sequence wherein a portion of said nucleotide sequence can be amplified by PCR using the primer pair of SEQ ID NO. 29 and SEQ ID NO. 33; and (i) said toxin comprises an amino acid sequence which has at least about 60% homology with an amino acid sequence selected from the group consisting of SEQ ID NO. 3, SEQ ID NO. 5, SEQ ID NO. 7, pesticidal portions of SEQ ID NO. 32, pesticidal portions of SEQ ID NO. 36, and pesticidal portions of SEQ ID NO. 41.

As used herein "stringent" conditions for hybridization refers to conditions which achieve the same, or about the same, degree of specificity of hybridization as the conditions employed by the current applicants. Specifically, hybridization of immobilized DNA on Southern blots with 32P-labeled gene-specific probes was performed by standard methods (Maniatis, T., E. F. Fritsch, J. Sambrook [1982] *Molecular Cloning: A Laboratory Manual,* Cold Spring Harbor Laboratory, Cold Spring Harbor, N.Y.). In general, hybridization and subsequent washes were carried out under stringent conditions that allowed for detection of target sequences with homology to the PS80JJ1 toxin genes. For double-stranded DNA gene probes, hybidization was carried out overnight at 20–25° C. below the melting temperature (Tm) of the DNA hybrid in 6X SSPE, 5X Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology,* R. Wu., L. Grossman and K. Moldave [eds.] Academic Press, New York 100:266–285).

Tm=81.5° C.+16.6 Log[Na+]+0.41(% G+C)−0.61(% formamide)−600/length of duplex in base pairs.

Washes are typically carried out as follows:

(1) Twice at room temperature for 15 minutes in 1X SSPE, 0.1% SDS (low stringency wash).

(2) Once at Tm−20° C. for 15 minutes in 0.2X SSPE, 0.1% SDS (moderate stringency wash).

For oligonucleotide probes, hybridization was carried out overnight at 10–20° C. below the melting temperature (Tm) of the hybrid in 6X SSPE, 5X Denhardt's solution, 0.1% SDS, 0.1 mg/ml denatured DNA. Tm for oligonucleotide probes was determined by the following formula:

Tm(°C.)=2(number T/A base pairs)+4(number G/C base pairs)

(Suggs, S. V., T. Miyake, E. H. Kawashime, M. J. Johnson, K. Itakura, and R. B. Wallace [1981] *ICN-UCLA Symp. Dev. Biol. Using Purified Genes,* D. D. Brown [ed.], Academic Press, New York, 23:683–693).

Washes were typically carried out as follows:

(1) Twice at room temperature for 15 minutes 1X SSPE, 0.1% SDS (low stringency wash).

(2) Once at the hybridization temperature for 15 minutes in 1X SSPE, 0.1% SDS (moderate stringency wash).

With the teachings provided herein, one skilled in the art could readily produce and use the various toxins and polynucleotide sequences of the novel classes described herein.

Microorganisms useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the deposited strains are as follows:

| Culture | Repository No. | Deposit Date |
| --- | --- | --- |
| B.t. strain PS80JJ1 | NRRL B-18679 | July 17, 1990 |
| B.t. strain PS149B1 | NRRL B-21553 | March 28, 1996 |
| B.t strain PS167H2 | NRRL B-21554 | March 28, 1996 |
| *E. coli* NM522 (pMYC2365) | NRRL B-21170 | January 5, 1994 |
| *E. coli* NM522 (pMYC2382) | NRRL B-21329 | September 28, 1994 |
| *E. coli* NM522 (pMYC2379) | NRRL B-21155 | November 3, 1993 |
| *E. coli* NM522 (pMYC2421) | NRRL B-21555 | March 28, 1996 |
| *E. coli* NM522 (pMYC2427) | NRRL B-21672 | March 26, 1997 |
| *E. coli* NM522 (pMYC2429) | NRRL B-21673 | March 26, 1997 |
| *E. coli* NM522 (pMYC2426) | NRRL B-21671 | March 26, 1997 |

The PS80JJ1 isolate is available to the public by virtue of the issuance of the U.S. Pat. No. 5,151,363.

B.t. isolates PS149B1 and PS167H2 have been deposited under conditions that assure that access to the cultures will be available during the pendency of this patent application to one determined by the Commissioner of Patents and Trademarks to be entitled thereto under 37 CRF 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit (s) should the depository be unable to furnish a sample when requested, due to the condition of the deposit(s). All restrictions on the availability to the public of the subject culture deposits will be irrevocably removed upon the granting of a patent disclosing them.

Following is a table which provides characteristics of certain B.t. isolates useful according to the subject invention.

TABLE 1

Description of B.t. strains toxic to coleopterans

| Culture | Crystal Description | Approx. MW (kDa) | Serotype | NRRL Deposit | Deposit Date |
|---|---|---|---|---|---|
| PS80JJ1 | multiple attached | 130, 90, 47, 37, 14 | 4a4b, sotto | B-18679 | 7-17-90 |
| PS149B1 | | 130, 47, 14 | | B-21553 | 3-28-96 |
| PS167H2 | | 70, 47, 14 | | B-23554 | 3-28-96 |

Genes and Toxins

The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or fragments of these toxins, can readily be prepared using standard procedures in this art. The gene which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) *DNA Probes*, Stockton Press, New York, N.Y., pp. 169–170. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxins. Equivalent toxins will have amino acid homology with an exemplified toxin. The amino acid identify will typically be greater than 60%, preferably be greater than 75%, more preferably greater than 80%, more preferably greater than 90%, and can be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |

TABLE 2-continued

| Class of Amino Acid | Examples of Amino Acids |
| --- | --- |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and locations of toxin inclusions, which are described above.

Recombinant Hosts

The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Control of coleopterans, including corn rootworm using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B.t., *E. coli,* or Pseudomonas. Transformations can be made by those skilled in the art using standard techniques. Materials necessary for these transformations are disclosed herein or are otherwise readily available to the skilled artisan.

Synthetic genes which are functionally equivalent to the toxins of the subject invention can also be used to transform hosts. Methods for the production of synthetic genes can be found in, for example, U.S. Pat. No. 5,380,831.

Control of other pests such as lepidopterans and other insects, nematodes, and mites can also be accomplished by those skilled in the art using standard techniques combined with the teachings provided herein.

Treatment of Cells

As mentioned above, B.t. or recombinant cells expressing a B.t. toxin can be treated to prolong the toxin activity and stabilize the cell. The pesticide microcapsule that is formed comprises the B.t. toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques,* W.H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. No. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handlink, economics, storage stability, and the like.

Growth of Cells

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrage, granules or other formulations by the addition of surfactants, dispersants, inert carriers, and other components to facilitate handling and application for particular target pests. These formulations and application procedures are all well known in the art.

Formulations

Formulated bait granules containing an attractant and spores and crystals of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rehological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Mutants

Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus (–). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Following are examples which illustrate procedures for practicing the invention. These examples should not be construed as limiting. All percentages are by weight and all solvent mixture proportions are by volume unless otherwise noted.

EXAMPLE 1

Culturing of B.t. Isolates of the Invention

A subculture of the B.t. isolates, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Protein Purification for 45 kDa 80JJ1 Protein

One gram of lyophilized powder of 80JJ1 was suspended in 40 ml of buffer containing 80 mM Tris-Cl pH 7.8, 5 mM EDTA, 100 μM PMSF, 0.5 μg/ml Leupeptin, 0.7 μg/ml Pepstatin, and 40 μg/ml Bestatin. The suspension was centrifuged, and the resulting supernatant was discarded. The pellet was washed five times using 35–40 ml of the above buffer for each wash. The washed pellet was resuspended in 10 ml of 40% NaBr, 5 mM EDTA, 100 μM PMSF, 0.5 μg/ml Leupeptin, 0.7 μg/ml Pepstatin, and 40 μg/ml Bestatin and placed on a rocker platform for 75 minutes. The NaBr suspension was centrifuged, the supernatant was removed, and the pellet was treated a second time with 40% NaBr, 5 mM EDTA, 100 μM PMSF, 0.5 μg/ml Leupeptin, 0.7 μg/ml Pepstatin, and 40 μg/ml Bestatin as above. The supernatants (40% NaBr soluble) were combined and dialyzed against 10 mM CAPS pH 10.0, 1 mM EDTA at 4° C. The dialyzed extracts were centrifuged and the resulting supernatant was removed. The pellet (40% NaBr dialysis pellet) was suspended in 5 ml of $H_2O$ and centrifuged. The resultant supernatant was removed and discarded. The washed pellet was washed a second time in 10 ml of $H_2O$ and centrifuged as above. The washed pellet was suspended in 1.5 ml of $H_2O$ and contained primarily three peptides with molecular weights of approximately 47 kDa, 45 kDa, and 15 kDa when analyzed using SDS-PAGE. At this stage of purification, the suspended 40% NaBr dialysis pellet contained approximately 21 mg/ml of protein by Lowry assay.

The peptides in the pellet suspension were separated using SDS-PAGE (Laemlli, U.K. [1970] *Nature* 227:680) in 15% acrylamide gels. The separated proteins were then electrophoretically blotted to a PVDF membrane (Millipore Corp.) in 10 mM CAPS pH 11.0, 10% MeOH at 100 V constant. After one hour the PVDF membrane was rinsed in water briefly and placed for 3 minutes in 0.25% Coomassie blue R-250, 50% methanol, 5% acetic acid. The stained membrane was destained in 40% MeOH, 5% acetic acid. The destained membrane was air-dried at room temperature (LeGendre et al. [1989] In *A practical Guide to Protein Purification For Microsequencing,* P. Matsudaira, ed. Academic Press, New York, N.Y.). The membrane was sequenced using automated gas phase Edman degradation (Hunkapillar, M. W., R. M. Hewick, W. L. Dreyer, L. E. Hood [1983] *Meth. Enzymol.* 91:399).

The amino acid analysis revealed that the N-terminal sequence of the 45 kDa band was as follows: Met-Leu-Asp-Thr-Asn (SEQ ID NO. 1).

The 47 kDa band was also analyzed and the N-terminal amino acid sequence was determined to be the same 5-amino acid sequence as SEQ ID NO. 1. Therefore, the N-terminal amino acid sequences of the 47 kDa peptide and the 45 kDa peptide were identical.

This amino acid sequence also corresponds to a sequence obtained from a 45 kDa peptide obtained from PS80JJ1 spore/crystal powders, using another purification protocol, with the N-terminal sequence as follows: Met-Leu-Asp-Thr-Asn-Lys-Val-Tyr-Glu-Ile-Ser-Asn-Leu-Ala-Asn-Gly-Leu-Tyr-Thr-Ser-Thr-Tyr-Leu-Ser-Leu (SEQ ID NO. 2).

EXAMPLE 3

Purification of the 14 kDa Peptide of PS80JJ1

0.8 ml of the white dialysis suspension (approximately 21 mg/ml) containing the 47 kDa, 45 kDa, and 15 kDa peptides, was dissolved in 10 ml of 40% NaBr, and 0.5 ml of 100 mM EDTA were added. After about 18 hours (overnight), a white opaque suspension was obtained. This was collected by centrifugation and discarded. The supernatant was concentrated in a Centricon-30 (Amicon Corporation) to a final volume of approximately 15 ml. The filtered volume was washed with water by filter dialysis and incubated on ice, eventually forming a milky white suspension. The suspension was centrifuged and the pellet and supernatant were separated and retained. The pellet was then suspended in 1.0 ml water (approximately 6 mg/ml). The pellet contained substantially pure 15 kDa protein when analyzed by SDS-PAGE.

The N-terminal amino acid sequence was determined to be: Ser-Ala-Arg-Glu-Val-His-Ile-Glu-Ile-Asn-Asn-Thr-Arg-His-Thr-Leu-Gln-Leu-Glu-Ala-Lys-Thr-Lys-Leu (SEQ ID NO. 3).

EXAMPLE 4

Protein Purification and Characterization of PS149B1 45 kDa Protein

The P1 pellet was resuspended with two volumes of deionized water per unit wet weight, and to this was added nine volumes of 40% (w/w) aqueous sodium bromide. This and all subsequent operations were carried out on ice or at 4–6° C. After 30 minutes, the suspension was diluted with 36 volumes of chilled water and centrifuged at 25,000×g for 30 minutes to give a pellet and a supernatant.

The resulting pellet was resuspended in 1–2 volumes of water and layered on a 20–40% (w/w) sodium bromide gradient and centrifuged at 8,000×g for 100 minutes. The layer banding at approximately 32% (w/w) sodium bromide (the "inclusions", or INC) was recovered and dialyzed overnight against water using a dialysis membrane with a 6–8 kDa MW cut-off. Particulate material was recovered by centrifugation at 25,000×g, resuspended in water, and aliquoted and assayed for protein by the method of Lowry and by SDS-PAGE.

The resulting supernatant was concentrated 3- to 4-fold using Centricon-10 concentrators, then dialyzed overnight against water using a dialysis membrane with a 6–8 kDa MW cut-off. Particulate material was recovered by centrifugation at 25,000×g, resuspended in water, and aliquoted and assayed for protein by the method of Lowry and by SDS-PAGE. This fraction was denoted as P1.P2.

The peptides in the pellet suspension were separated using SDS-PAGE (Laemlli, U.K., supra) in 15% acrylamide gels. The separated proteins were then electrophoretically blotted to a PVDF membrane (Millipore Corp.) in 10 mM CAPS pH 11.0, 10% MeOH at 100 V constant. After one hour the PVDF membrane was rinsed in water briefly and placed for 3 minutes in 0.25% Coomassie blue R-250, 50% methanol, 5% acetic acid. The stained membrane was destained in 40% MeOH, 5% acetic acid. The destained membrane was air-dried at room temperature (LeGendre et al., supra). The membrane was sequenced using automated gas phase Edman degradation (Hunkapillar et al., supra).

Protein analysis indicated the presence of two major polypeptides, with molecular weights of 47 kDa and 14 kDa. Molecular weights were measured against standard polypeptides of known molecular weight. This process provides only an estimate of true molecular weight. The 47 kDa band from PS149B1 migrated on SDS-PAGE in a manner indistinguishable from the 47 kDa protein from PS80JJ1. Likewise, the 14 kDa band from PS149B1 migrated on SDS-PAGE in a manner indistinguishable from 14 kDa bands from PS167H2 and PS80JJ1. Apart from these two polypeptides, which were estimated to account for 25–35% (47 kDa) and 35–55% (15 kDa) of the Coomassie staining material respectively, there may be minor bands, including those of estimated MW at 46 kDa, 130 kDa, and 70 kDa.

Protein analysis indicated that fraction INC contained a single polypeptide with MW of 47 kDa, and that fraction P1.P2 contained a single polypeptide with MW of 14 kDa. These polypeptides were recovered in yields greater than 50% from P1.

The N-terminal amino acid sequence for the purified 47 kDa protein from PS149B1 is: Met-Leu-Asp-Thr-Asn-Lys-Val-Tyr-Glu-Ile-Ser-Asn-His-Ala-Asn-Gly-Leu-Tyr-Ala-Ala-Thr-Tyr-Leu-Ser-Leu (SEQ ID NO. 4).

The N-terminal amino acid sequence for the purified 14 kDa protein from PS149B1 is: Ser-Ala-Arg-Glu-Val-His-Ile-Asp-Val-Asn-Asn-Lys-Thr-Gly-His-Thr-Leu-Gln-Leu-Glu-Asp-Lys-Thr-Lys-Leu-Asp-Gly-Gly-Arg-Trp-Arg-Thr-Ser-Pro-Xaa-Asn-Val-Ala-Asn-Asp-Gln-Ile-Lys-Thr-Phe-Val-Ala-Glu-Ser-Asn (SEQ ID NO.5).

EXAMPLE 5

Amino Acid Sequence for 45 kDa and 14 kDa Toxins of PS167H2

The N-terminal amino acid sequence for the purified 45 kDa protein from PS167H2 is: Met-Leu-Asp-Thr-Asn-Lys-Ile-Tyr-Glu-Ile-Ser-Asn-Tyr-Ala-Asn-Gly-Leu-His-Ala-Ala-Thr-Tyr-Leu-Ser-Leu (SEQ ID NO. 6).

The N-terminal amino acid sequence for the purified 14 kDa protein from PS167H2 is: Ser-Ala-Arg-Glu-Val-His-Ile-Asp-Val-Asn-Asn-Lys-Thr-Gly-His-Thr-Leu-Gln-Leu-Glu-Asp-Lys-Thr-Lys-Leu (SEQ ID NO. 7).

These amino acid sequences can be compared to the sequence obtained for the 47 kDa peptide obtained from 80JJ1 spore/crystal powders with the N-terminal sequence (SEQ ID NO. 1) and to the sequence obtained for the 14 kDa peptide obtained from 80JJ1 spore/crystal powders with the N-terminal sequence (SEQ ID NO. 3).

Clearly, the 45–47 kDa proteins are highly related and probably represent one gene family, and the 14 kDa proteins are highly related and probably represent another gene family.

EXAMPLE 6

Molecular Cloning, Expression, and DNA Sequence Analysis of a Novel δ-Endotoxin Gene from *Bacillus thuringiensis* Strain PS80JJ1

Total cellular DNA was prepared from *Bacillus thuringiensis* (B.t.) cells grown to an optical density, at 600 nm, of 1.0. Cells were pelleted by centrifugation and resuspended in protoplast buffer (20 mg/ml lysozyme in 0.3 M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE buffer.

An oligonucleotide probe for the gene encoding the PS80JJ1 45 kDa toxin was designed from N-terminal peptide sequence data. The sequence of the 29-base oligonucleotide probe was:

5'-ATG YTW GAT ACW AAT AAA GTW TAT GAA AT-3' (SEQ ID NO. 8)

This oligonucleotide was mixed at four positions as shown. This probe was radiolabeled with $^{32}P$ and used in standard condition hybridization of Southern blots of PS80JJ1 total cellular DNA digested with various restriction endonucleases. Representative autoradiographic data from these experiments showing the sizes of DNA restriction fragments containing sequence homology to the 44.3 kDa toxin oligonucleotide probe of SEQ ID NO. 8 are presented in Table 3.

TABLE 3

RFLP of PS80JJ1 cellular DNA fragments on Southern blots that hybridized under standard conditions with the 44.3 kDa toxin gene oligonucleotide probe (SEQ ID NO. 8)

| Restriction Enzyme | Approximate Fragment Size (kbp) |
|---|---|
| EcoRI | 6.0 |
| HindIII | 8.3 |
| KpnI | 7.4 |
| PstI | 11.5 |
| XbaI | 9.1 |

These DNA fragments identified in these analyses contain all or a segment of the PS80JJ1 45 kDa toxin gene. The approximate sizes of the hybridizing DNA fragments in Table 3 are in reasonable agreement with the sizes of a subset of the PS80JJ1 fragments hybridizing with a PS80JJ1 45 kDa toxin subgene probe used in separate experiments, as predicted (see Table 4, below).

A gene library was constructed from PS80JJ1 DNA partially digested with Sau3AI. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The Sau3AI inserts were ligated into BamHI-digested LambdaGem-11 (Promega, Madison, Wis.). Recombinant phage were packaged and plated on E. coli KW251 cells. Plaques were screened by hybridization wit the oligonucleotide probe described above. Hybridizing phage were plaque-purified and used to infect liquid cultures of E. coli KW251 cells for isolation of DNA by standard procedures (Maniatis et al., supra).

Southern blot analysis revealed that one of the recombinant phage isolates contained an approximately 4.8 kbp XbaI-SacI band that hybridized to the PS80JJ1 toxin gene probe. The SacI site flanking the PS80JJ1 toxin gene is a phage vector cloning site, while the flanking XbaI site is located within the PS80JJ1 DNA insert. This DNA restriction fragment was subcloned by standard methods into pBluescript S/K (Stragagene, San Diego, Calif.) for sequence analysis. The resultant plasmid was designated pMYC2421. The DNA insert was also subcloned into pHT-BlueII (an E. coli/B. thuringiensis shuttle vector comprised of pBluescript S/K [Stratagene, La Jolla, Calif.] and the replication origin from a resident B.t. plasmid [D. Lereclus et al. (1989) FEMS Microbiology Letters 60:211–218]) to yield pMYC2420.

An oligonucleotide probe for the gene encoding the PS80JJ1 14 kDa toxin was designed from N-terminal peptide sequence data. The sequence of the 28-base oligonucleotide probe was: 5'GW GAA GTW CAT ATW GAA ATW AAT AAT AC 3' (SEQ ID NO. 29). This oligonucleotide was mixed at four positions as shown. The probe was radiolabelled with $^{32}P$ and used in standard condition hybridizations of Southern blots of PS80JJ1 total cellular and pMYC2421 DNA digested with various restriction endonucleases. These RFLP mapping experiments demonstrated that the gene encoding the 14 kDa toxin is located on the same genomic EcoRI fragment that contains the N-terminal coding sequence for the 44.3 kDa toxin.

To test expression of the PS80JJ1 toxin genes in *B.t.,* pMYC2420 was transformed into the acrystalliferous (Cry-) *B.t.* host, CryB (A. Aronson, Purdue University, West Lafayette, Ind.), by electroporation. Expression of both the approximately 14 and 44.3 kDa PS80JJ1 toxins encoded by pMYC2420 was demonstrated by SDS-PAGE analysis. Toxin crystal preparations from the recombinant CryB [pMYC2420] strain, MR536, were assayed and found to be active against western corn rootworm.

The PS80JJ1 toxin genes encoded by pMYC2421 were sequenced using the ABI373 automated sequencing system and associate software. The sequence of the entire genetic locus containing both open reading frames and flanking nucleotide sequences is shown in SEQ ID NO. 30. The termination codon of the 14 kDa toxin gene is 121 base pairs upstream (5') from the initiation codon of the 44.3 kDa toxin gene (FIG. 2). The PS80JJ1 14 kDa toxin open reading frame nucleotide sequence (SEQ ID NO. 31), the 44.3 kDa toxin open reading frame nucleotide sequence (SEQ ID NO. 10), and the respective deduced amino acid sequences (SEQ ID NO. 32 and SEQ ID NO. 11) are novel compared to other toxin genes encoding pesticidal proteins.

Thus, the nucleotide sequence encoding the 14 kDa toxin of PS80JJ1 is shown in SEQ ID NO. 31. The deduced amino acid sequence of the 14 kDa toxin of PS80JJ1 is shown in SEQ ID NO. 32. The nucleotide sequences encoding both the 14 and 45 kDa toxins of PS80JJ1, as well as the flanking sequences, are shown in SEQ ID NO. 30. The relationship of these sequences is shown in FIG. 2.

A subculture of *E. coli* NM522 containing plasmid pMYC2421 was deposited in the permanent collection of the Patent Culture Collection (NRRL), Regional Research Center, 1815 North University Street, Peoria, Ill. 61604 USA on Mar. 28, 1996. The accession number is NRRL B-21555.

EXAMPLE 7

RFLP and PCR Analysis of Additional Novel δ-Endotoxin Genes from *Bacillus thuringiensis* Strains PS149B1 and PS167H2

Two additional strains active against corn rootworm, PS149B1 and PS167H2, also produce parasporal protein crystals comprised in part of polypeptides approximately 14 and 45 kDa in size. Southern hybridization and partial DNA sequence analysis were used to examine the relatedness of these toxins to the PS80JJ1 toxins. DNA was extracted from these *B.t.* strains as described above, and standard Southern hybridizations were performed using the 14 kDa toxin oligonucleotide probe (SEQ ID NO. 29) and an approximately 800 bp PCR fragment of the PS80JJ1 44.3 kDa toxin gene-encoding sequence. Representative RFLP data from these experiments showing the sizes of DNA restriction fragments containing sequence homology to the 44.3 kDa toxin are presented in Table 4. Representative RFLP data from these experiments showing the sizes of DNA restriction fragments containing sequence homology to the approximately 14 kDa toxin are presented in Table 5.

TABLE 4

RFLP of PS80JJ1, PS149B1, and PS167H2 cellular DNA fragments on Southern blots that hybridized with the approximately 800 bp PS80JJ1 44.3 kDa toxin subgene probe under standard conditions

| Restriction enzyme | PS80JJ1 | PS149B1 | PS167H2 |
|---|---|---|---|
| | Strain: Approximate fragment size (kbp) | | |
| EcoRI | 6.4 | 5.7 | 2.6 |
| | 1.3 | 2.8 | |
| | 0.6 | | |
| HindIII | 8.2 | 6.2 | 4.4 |
| KpnI | 7.8 | 10.0 | 11.5 |
| PstI | 12.0 | 9.2 | 9.2 |
| | | | 8.2 |
| XbaI | 9.4 | 10.9 | 10.9 |
| SacI | 17.5 | 15.5 | 11.1 |
| | 13.1 | 10.5 | 6.3 |

Each of the three strains exhibited unique RFLP patterns. The hybridizing DNA fragments from PS149B1 or PS167 H2 contain all or part of toxin genes with sequence homology to the PS80JJ1 44.3 kDa toxin.

TABLE 5

Restriction fragment length polymorphisms of PS80JJ1, PS149B1, and PS167H2 cellular DNA fragments on Southern blots that hybridized with the PS80JJ1 14 kDa toxin oligonucleotide probe under standard conditions

| | Strain | | |
|---|---|---|---|
| | PS80JJ1 | PS149B1 | PS167H2 |
| Restriction enzyme | Approximate fragment size (kbp) | | |
| EcoRI | 5.6 | 2.7 | 2.7 |
| HindIII | 7.1 | 6.0 | 4.7 |
| XbaI | 8.4 | 11.2 | 11.2 |

Each of the three strains exhibited unique RFLP patterns. The hybridizing DNA fragments from PS149B1 or PS167H2 contain all or part of toxin genes with sequence homology to the PS80JJ1 14 kDa toxin gene.

Portions of the toxin genes in PS149B1 or PS167H2 were amplified by PCR using forward and reverse oligonucleotide primer pairs designed based on the PS80JJ1 44.3 kDa toxin gene sequence. For PS149B1, the following primer pair was used:

```
Forward:
5'-ATG YTW GAT ACW AAT AAA GTW TAT GAA AT-3'   (SEQ ID NO. 8)
Reverse:
5'-GGA TTA TCT ATC TCT GAG TGT TCT TG-3'        (SEQ ID NO. 9)
```

For PS167H2, the same primer pair was used. These PCR-derived fragments were sequenced using the ABI373 automated sequencing system and associated software. The partial gene and peptide sequences obtained are shown in SEQ ID NO. 12–15. These sequences contain portions of the nucleotide coding sequences and peptide sequences for novel corn rootworm-active toxins present in B.t. strains PS149B1 or PS167H2.

EXAMPLE 8

Molecular Cloning and DNA Sequence Analysis of Novel δ-Endotoxin Genes from *Bacillus thuringiensis* Strains PS149B1 and PS167H2

Total cellular DNA was extracted from strains PS149B1 and PS167H2 as described for PS80JJ1. Gene libraries of size-fractionated Sau3A partial restriction fragments were constructed in Lambda-Gem11 for each respective strain as previously described. Recombinant phage were packaged and plated on *E. coli* KW251 cells. Plaques were screened by hybridization with the oligonucleotide probe specific for the 44 kDa toxin gene. Hybridizing phage were plaque-purified and used to infect liquid cultures of *E. coli* KW251 cells for isolation of DNA by standard procedures (Maniatis et al., supra).

For PS167H2, Southern blot analysis revealed that one of the recombinant phage isolates contained an approximately 4.0 to 4.4 kbp HindIII band that hybridized to the PS80JJ1 44 kDa toxin gene 5' oligonucleotide probe (SEQ ID NO. 8). This DNA restriction fragment was subcloned by standard methods into pBluescript S/K (Stratgene, San Diego, Calif.) for sequence analysis. The fragment was also subcloned into the high copy number shuttle vector, pHT370 (Arantes, O., D. Lereclus [1991] *Gene* 108:115–119) for expression analyses in *Bacillus thuringiensis* (see below). The resultant recombinant, high copy number bifunctional plasmid was designated pMYC2427.

The PS167H2 toxin genes encoded by pMYC2427 were sequenced using the ABI automated sequencing system and associated software. The sequence of the entire genetic locus containing both open reading frames and flanking nucleotide sequences is shown in SEQ ID NO. 34. The termination codon of the 14 kDa toxin gene is 107 base pairs upstream (5') from the initiation codon of the 44 kDa toxin gene. The PS167H2 14 kDa toxin coding sequence (SEQ ID NO. 35), the 44 kDa toxin coding sequence (SEQ ID NO. 37), and the respective deduced amino acid sequences, SEQ ID NO. 36 and SEQ ID NO. 38, are novel compared to other known toxin genes encoding pesticidal proteins. The toxin genes are arranged in a similar manner to, and have some homology with, the PS80JJ1 14 and 44 kDa toxins.

A subculture of *E. coli* NM522 containing plasmid pMYC2427 was deposited in the permanent collection of the Patent Culture Collection (NRRL), Regional Research Center, 1815 North University Street, Peoria, Ill. 61604 USA on Mar. 26, 1997. The accession number is NRRL B-21672.

For PS149B1, Southern blot analysis using the PS80JJ1 44 kDa oligonucleotide 5' probe (SEQ ID NO. 8) demonstrated hybridization of an approximately 5.9 kbp ClaI DNA fragment. Complete ClaI digests of PS149B1 genomic DNA were size fractionated on agarose gels and cloned into pHTBlueII. The fragment was also subcloned into the high copy number shuttle vector, pHT370 (Arantes, O., D. Lerclus [1991] *Gene* 108:115–119) for expression analyses in *Bacillus thuringiensis* (see below). The resultant recombinant, high copy number bifunctional plasmid was designated pMYC2429.

The PS149B1 toxin genes encoded by pMYC2429 were sequenced using the ABI automated sequencing system and associated software. The sequence of the entire genetic locus containing both open reading frames and flanking nucleotide sequences is shown in SEQ ID NO. 39. The termination codon of the 14 kDa toxin gene is 108 base pairs upstream (5') from the initiation codon of the 44 kDa toxin gene. The PS149B1 14 kDa toxin coding sequence (SEQ ID NO. 40), the 44 kDa toxin coding sequence (SEQ ID NO. 42), and the respective deduced amino acid sequences, SEQ ID NO. 41 and SEQ ID NO. 43, are novel compared to other known toxin genes encoding pesticidal proteins. The toxin genes are arranged in a similar manner as, and have some homology with, the PS80JJ1 and PS167H2 14 and 44 kDa toxins. Together, these three toxin operons comprise a new family of pesticidal toxins.

A subculture of *E. coli* NM522 containing plasmid pMYC2429 was deposited in the permanent collection of the Patent Culture Collection (NRRL), Regional Research Center, 1815 North University Street, Peoria, Ill. 61604 USA on Mar. 26, 1997. The accession number is NRRL B-21673.

EXAMPLE 9

PCR Amplification for Identification and Cloning Novel Corn Rootworm-Active Toxin The DNA and peptide sequences of the three novel approximately 45 kDa corn rootworm-active toxins from PS80JJ1, PS149B1, and PS167H2 (SEQ ID NOS. 12–15)

were aligned with the Genetics Computer group sequence analysis program Pileup using a gap weight of 3.00 and a gap length weight of 0.10. The sequence alignments were used to identify conserved peptide sequences to which oligonucleotide primers were designed that were likely to hybridize to genes encoding members of this novel toxin family. Such primers can be used in PCR to amplify diagnostic DNA fragments for these and related toxin genes. Numerous primer designs to various sequences are possible, four of which are described here to provide an example. These peptide sequences are:

| | |
|---|---|
| Asp-Ile-Asp-Asp-Tyr-Asn-Leu | (SEQ ID NO. 16) |
| Trp-Phe-Leu-Phe-Pro-Ile-Asp | (SEQ ID NO. 17) |
| Gln-Ile-Lys-Thr-Thr-Pro-Tyr-Tyr | (SEQ ID NO. 18) |
| Tyr-Glu-Trp-Gly-Thr-Glu. | (SEQ ID NO. 19) |

The corresponding nucleotide sequences are:

| | |
|---|---|
| 5'-GATATWGATGAYTAYAAYTTR-3' | (SEQ ID NO. 20) |
| 5'-TGGTTTTTRTTTCCWATWGAY-3' | (SEQ ID NO. 21) |
| 5'-CAAATHAAAACWACWCCATATTAT-3' | (SEQ ID NO. 22) |
| 5'-TAYGARTGGGGHACAGAA-3'. | (SEQ ID NO. 23) |

Forward primers for polymerase amplification in thermocycle reactions were designed based on the nucleotide sequences of SEQ ID NOS. 20 and 21.

Reverse primers were designed based on the reverse complement of SEQ ID NOS. 22 and 23:

| | |
|---|---|
| 5'-ATAATATGGWGTWGTTTTDATTTG-3' | (SEQ ID NO. 24) |
| 5'-TTCTGTDCCCCAYTCRTA-3'. | (SEQ ID NO. 25) |

These primers can be used in combination to amplify DNA fragments of the following sizes (Table 6) that identify genes encoding novel corn rootworm toxins.

TABLE 6

Predicted sizes of diagnostic DNA fragments (base pairs) amplifiable with primers specific for novel corn rootworm-active toxins

| Primer pair (SEQ ID NO.) | DNA fragment size (bp) |
|---|---|
| 20 + 24 | 495 |
| 20 + 25 | 594 |
| 21 + 24 | 471 |
| 21 + 25 | 580 |

Similarly, entire genes encoding novel corn rootworm-active toxins can be isolated by polymerase amplification in thermocycle reactions using primers designed based on DNA sequences flanking the open reading frames. For the PS80JJ1 44.3 kDa toxin, one such primer pair was designed, synthesized, and used to amplify a diagnostic 1613 bp DNA fragment that included the entire toxin coding sequence. These primers are:

| | |
|---|---|
| Forward: 5'-CTCAAAGCGGATCAGGAG-3' | (SEQ ID NO. 26) |
| Reverse: 5'-GCGTATTCGGATATGCTTGG-3'. | (SEQ ID NO. 27) |

For PCR amplification of the PS80JJ1 14 kDa toxin, the oligonucleotide coding for the N-terminal peptide sequence (SEQ ID NO. 29) can be used in combination with various reverse oligonucleotide primers based on the sequences in the PS80JJ1 toxin gene locus. One such reverse primer has the following sequence:

5' CATGAGATTTATCTCCTGATCCGC 3'  (SEQ ID NO. 33).

When used in standard PCR reactions, this primer pair amplified a diagnostic 1390 bp DNA fragment that includes the entire 14 kDa toxin coding sequence and some 3' flanking sequences corresponding to the 121 base intergenic spacer and a portion of the 44.3 kDa toxin gene. When used in combination with the 14 kDa forward primer, PCR will generate a diagnostic 322 base pair DNA fragment.

EXAMPLE 10

Bioassay of Protein

A preparation of the insoluble fraction from the dialyzed NaBr extract of PS80JJ1 containing the 47 kDa, 45 kDa, and 15 kDa peptides was bioassayed against Western corn rootworm and found to exhibit significant toxin activity.

EXAMPLE 11

Bioassay of Protein

The purified protein fractions from PS149B1 were bioassayed against western corn rootworm and found to exhibit significant toxin activity when combined. In fact, the combination restored activity to that noted in the original preparation (P1). The following bioassay data set presents percent mortality and demonstrates this effect.

TABLE 7

| Concentration ($\mu g/cm^2$) | P1 | INC | P1.P2 | INC + P1.P2 |
|---|---|---|---|---|
| 300 | 88, 100, 94 | 19 | 13 | 100 |
| 100 | 94, 50, 63 | 31 | 38 | 94 |
| 33.3 | 19, 19, 44 | 38 | 13 | 50 |
| 11.1 | 13, 56, 25 | 12 | 31 | 13 |
| 3.7 | 0, 50, 0 | 0 | 31 | 13 |
| 1.2 | 13, 43, 12 | 0 | 12 | 19 |
| 0.4 | 6, 12, 6 | 25 | 19 | 6 |

EXAMPLE 12

Clone Dose-Response Bioassays

The PS80JJ1 toxin operon was also subcloned from pMYC2421 into pHT370 for direct comparison of bioactivity with the recombinant toxins closed from PS149B1 and PS167H2. The resultant recombinant, high copy number bifunctional plasmid was designated pMYC2426.

A subculture of *E. coli* NM522 containing plasmid pMYC2426 was deposited in the permanent collection of the Patent Culture Collection (NRRL), Regional Research Center, 1815 North University Street, Peoria, Ill. 61604 USA on Mar. 26, 1997. The accession number is NRRL B-21671.

To test expression of the PS80JJ1, PS149B1 and PS167H2 toxin genes in *B.t.*, pMYC2426, pMYC2427 and pMYC2429 were separately transformed into the acrystalliferous(Cry-) *B.t.* host, CryB (A. Aronson, Purdue University, West Lafayette, Ind.), by electroporation. The recombinant strains were designated MR543 (CryB [pMYC2426]), MR544 (CryB [pMYC2427]) and MR546 (CryB [pMYC2429]), respectively. Expression of both the approximately 14 and 44 kDa toxins was demonstrated by SDS-PAGE analysis for each recombinant strain.

Toxin crystal preparations from the recombinant strains were assayed against western corn rootworm. Their diet was amended with sorbic acid and SIGMA pen-strep-ampho-B. The material was top-loaded at a rate of 50 µl of suspension per cm$^2$ diet surface area. Bioassays were run with neonate Western corn rootworm larvae for 4 days at approximately 25° C. Percentage mortality and top-load $LC_{50}$ estimates for the clones (pellets) are set forth in Table 8.

TABLE 8

| Sample | Percentage mortality at given protein concentration (µg/cm$^2$) | | |
|---|---|---|---|
| | 50 | 5 | 0.5 |
| MR543 pellet | 44 | 19 | 9 |
| MR544 pellet | 72 | 32 | 21 |
| MR546 pellet | 52 | 32 | 21 |
| dH2O | 7 | | |

EXAMPLE 13

Insertion and Expression of Toxin Genes Into Plants

One aspect of the subject invention is the transformation of plants with genes encoding the insecticidal toxin. The transformed plants are resistant to attack by the target pest.

The novel corn rootworm-active genes described here can be optimized for expression in other organisms. Maize optimized gene sequences encoding the 14 and 44 kDa PS80JJ1 toxins are disclosed in SEQ ID NO. 44 and SEQ ID NO. 45, respectively.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, et. Accordingly, the sequence encoding the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecularbiological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J*. 4:277–287.

Once the inserted DNA has been integrated in the genome, it is relatively stable there and, as a rule, does not come out again. It normally contains a section marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection biolistics (miocroparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet*. 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic *B.t.* genes for use in plants are known in the art.

EXAMPLE 14

Cloning of *B.t.* Genes Into Insect Viruses

A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An isolated polynucleotide which encodes a Bacillus toxin active against a non-mammalian pest, wherein said toxin has a molecular weight between approximately 10 kDa and approximately 15 kDa toxin, and wherein a nucleotide sequence selected from the group consisting of SEQ ID NO. 29, SEQ ID NO. 31, SEQ ID NO. 33, SEQ ID NO. 35, SEQ ID NO. 40, and SEQ ID NO. 44 hybridizes under stringent conditions with said polynucleotide.

2. The polynucleotide according to claim 1 wherein said toxin is active against a coleopteran pest.

3. The polynucleotide according to claim 1 wherein said toxin is active against corn rootworm.

4. The polynucleotide according to claim 1 wherein said toxin is active against western corn rootworm.

5. The polynucleotide according to claim 2 wherein said nucleotide sequence is SEQ ID NO. 29.

6. The polynucleotide according to claim 2 wherein said nucleotide sequence is SEQ ID NO. 31.

7. The polynucleotide according to claim 2 wherein said nucleotide sequence is SEQ ID NO. 33.

8. The polynucleotide according to claim 2 wherein said nucleotide sequence is SEQ ID NO. 35.

9. The polynucleotide according to claim 2 wherein said nucleotide sequence is SEQ ID NO. 40.

10. The polynucleotide according to claim 2 wherein said nucleotide sequence is SEQ ID NO. 44.

11. An isolated polynucleotide comprising a nucleotide sequence which encodes a toxin active against a non-mammalian pest wherein said toxin comprises a pesticidal portion of an amino acid sequence encoded by the nucleotide sequence shown in the group selected from SEQ ID NO. 30, SEQ ID NO. 34, and SEQ ID NO. 39.

12. The polynucleotide according to claim 11 wherein said nucleotide sequence is SEQ ID NO. 30.

13. The polynucleotide according to claim 11 wherein said nucleotide sequence is SEQ ID NO. 34.

14. The polynucleotide according to claim 11 wherein said nucleotide sequence is SEQ ID NO. 39.

15. The polynucleotide according to claim 11 wherein said toxin comprises an amino acid sequence encoded by SEQ ID NO. 30.

16. The polynucleotide according to claim 11 wherein said toxin comprises an amino acid sequence encoded by SEQ ID NO. 34.

17. The polynucleotide according to claim 11 wherein said toxin comprises an amino acid sequence encoded by SEQ ID NO. 39.

18. The polynucleotide according to claim 11 wherein said toxin is approximately 10–15 kDa.

19. An isolated polynucleotide comprising a nucleotide sequence which encodes a toxin which is active against a non-mammalian pest, wherein said nucleotide sequence is from a *Bacillus thuringiensis* isolate selected from the group consisting of PS149B1, having the identifying characteristics of NRRL B-21553; and PS167H2, having the identifying characteristics of NRRL B-21554.

20. The isolated polynucleotide according to claim 19 wherein said toxin is approximately 10–15 kDa.

21. The isolated polynucleotide according to claim 19 wherein said isolate is PS149B1, having the identifying characteristics of NRRL B-21553.

22. The isolated polynucleotide according to claim 19 wherein said isolate is PS167H2, having the identifying characteristics of NRRL B-21554.

23. The isolated polynucleotide according to claim 21 wherein said toxin is approximately 10–15 kDa.

24. The isolated polynucleotide according to claim 22 wherein said toxin is approximately 10–15 kDa.

25. An isolated polynucleotide comprising a nucleotide sequence which encodes a toxin which is active against a non-mammalian pest, wherein said toxin is from *Bacillus thuringiensis* isolate PS80JJ1, having the identifying characteristics of NRRL B-18679; and wherein said toxin is approximately 10–15 kDa.

26. An isolated polynucleotide comprising a nucleotide sequence which encodes a toxin active against a non-mammalian pest wherein said toxin comprises a pesticidal portion of an amino acid sequence selected from the group consisting of SEQ ID NO. 32, SEQ ID NO. 36, and SEQ ID NO. 41.

27. The isolated polynucleotide, according to claim 26, wherein said toxin comprises the amino acid sequence shown in SEQ ID NO. 32.

28. The isolated polynucleotide, according to claim 26, wherein said nucleotide sequence encodes a toxin of approximately 10–15 kDa.

29. The polynucleotide of claim 26 wherein said toxin comprises a pesticidal portion of the amino acid sequence shown in SEQ ID NO. 32.

30. The polynucleotide of claim 26 wherein said toxin comprises a pesticidal portion of the amino acid sequence shown in SEQ ID NO. 36.

31. The polynucleotide of claim 26 wherein said toxin comprises a pesticidal portion of the amino acid sequence shown in SEQ ID NO. 41.

32. The isolated polynucleotide, according to claim 26, wherein said toxin comprises the amino acid sequence shown in SEQ ID NO. 36.

33. The isolated polynucleotide, according to claim 26, wherein said toxin comprises the amino acid sequence shown in SEQ ID NO. 41.

34. The polynucleotide of claim 26 wherein said polynucleotide comprises a nucleotide sequence selected from the group consisting of SEQ ID NO. 31, SEQ ID NO. 35, SEQ ID NO. 40, and fragments of the foregoing that are sufficient to encode an active toxin.

35. The polynucleotide of claim 26 wherein said polynucleotide comprises a fragment of SEQ ID NO. 31 that is sufficient to encode an active toxin.

36. The polynucleotide of claim 26 wherein said polynucleotide comprises the nucleotide sequence shown in SEQ ID NO. 31.

37. The polynucleotide of claim 26 wherein said polynucleotide comprises a fragment of SEQ ID NO. 35 that is sufficient to encode an active toxin.

38. The polynucleotide of claim 26 wherein said polynucleotide comprises the nucleotide sequence shown in SEQ ID NO. 35.

39. The polynucleotide of claim 26 wherein said polynucleotide comprises a fragment of SEQ ID NO. 40 that is sufficient to encode an active toxin.

40. The polynucleotide of claim 26 wherein said polynucleotide comprises the nucleotide sequence shown in SEQ ID NO. 40.

41. A polynucleotide comprising a nucleotide sequence which encodes an approximately 10–15 kDa 80JJ1 toxin active against a coleopteran pest, wherein said nucleotide sequence has been optimized for expression in plants, and wherein said toxin comprises the amino acid sequence shown in SEQ ID NO. 32.

42. An isolated polynucleotide that comprises the sequence shown in SEQ ID NO. 44.

43. A polynucleotide comprising a nucleotide sequence which encodes an approximately 10–15 kDa polypeptide, wherein said nucleotide sequence is optimized for expression in plants, and wherein said polypeptide comprises an amino acid sequence selected from the group consisting of SEQ ID NO. 36 and SEQ ID NO. 41.

44. The polynucleotide according to claim 43 wherein said amino acid sequence is SEQ ID NO. 36.

45. The polynucleotide according to claim 43 wherein said amino acid sequence is SEQ ID NO. 41.

46. A recombinant host that expresses at least a first polynucleotide, which encodes a first pesticidally active Bacillus polypeptide, and a second polynucleotide, which encodes a second pesticidally active Bacillus polypeptide, wherein said first polypeptide has a molecular weight between approximately 10 kDa and approximately 15 kDa, and wherein said first polynucleotide hybridizes under stringent conditions to a nucleotide sequence selected from the group consisting of SEQ ID NO: 29, SEQ ID NO: 31, SEQ ID NO: 33, SEQ ID NO: 35, SEQ ID NO: 40, and SEQ ID NO: 44; and wherein said second polypeptide has a molecular weight between approximately 40 kDa and approximately 50 kDa, and wherein said second polynucleotide hybridizes under stringent conditions to a nucleotide sequence selected from the group consisting of SEQ ID NO: 8, SEQ ID NO: 9, SEQ ID NO: 10, SEQ ID NO: 12; SEQ ID NO: 14, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 37, SEQ ID NO: 42 and SEQ ID NO: 45.

47. The recombinant host of claim 46 wherein said first polynucleotide hybridizes under stringent conditions to SEQ ID NO. 29.

48. The recombinant host of claim 46 wherein said first polynucleotide hybridizes under stringent conditions to SEQ ID NO. 31.

49. The recombinant host of claim 46 wherein said first polynucleotide hybridizes under stringent conditions to SEQ ID NO. 33.

50. The recombinant host of claim 46 wherein said first polynucleotide hybridizes under stringent conditions to SEQ ID NO. 35.

51. The recombinant host of claim 46 wherein said first polynucleotide hybridizes under stringent conditions to SEQ ID NO. 40.

52. The recombinant host of claim 46 wherein said first polynucleotide hybridizes under stringent conditions to SEQ ID NO. 44.

53. The recombinant host of claim 46 wherein said second polynucleotide hybridizes under stringent conditions to SEQ ID NO. 8.

54. The recombinant host of claim 46 wherein said second polynucleotide hybridizes under stringent conditions to SEQ ID NO. 9.

55. The recombinant host of claim 46 wherein said second polynucleotide hybridizes under stringent conditions to SEQ ID NO. 10.

56. The recombinant host of claim 46 wherein said second polynucleotide hybridizes under stringent conditions to SEQ ID NO. 12.

57. The recombinant host of claim 46 wherein said second polynucleotide hybridizes under stringent conditions to SEQ ID NO. 14.

58. The recombinant host of claim 46 wherein said second polynucleotide hybridizes under stringent conditions to SEQ ID NO. 20.

59. The recombinant host of claim 46 wherein said second polynucleotide hybridizes under stringent conditions to SEQ ID NO. 21.

60. The recombinant host of claim 46 wherein said second polynucleotide hybridizes under stringent conditions to SEQ ID NO. 22.

61. The recombinant host of claim 46 wherein said second polynucleotide hybridizes under stringent conditions to SEQ ID NO. 23.

62. The recombinant host of claim 46 wherein said second polynucleotide hybridizes under stringent conditions to SEQ ID NO. 24.

63. The recombinant host of claim 46 wherein said second polynucleotide hybridizes under stringent conditions to SEQ ID NO. 25.

64. The recombinant host of claim 46 wherein said second polynucleotide hybridizes under stringent conditions to SEQ ID NO. 26.

65. The recombinant host of claim 46 wherein said second polynucleotide hybridizes under stringent conditions to SEQ ID NO. 27.

66. The recombinant host of claim 46 wherein said second polynucleotide hybridizes under stringent conditions to SEQ ID NO. 37.

67. The recombinant host of claim 46 wherein said second polynucleotide hybridizes under stringent conditions to SEQ ID NO. 42.

68. The recombinant host of claim 46 wherein said second polynucleotide hybridizes under stringent conditions to SEQ ID NO. 45.

69. A recombinant host comprising a polynucleotide sequence which encodes a polypeptide comprising a pesticidal portion of an amino acid sequence selected from the group consisting of SEQ ID NO. 32, SEQ ID NO. 36, and SEQ ID NO. 41.

70. The recombinant host according to claim 69 wherein said amino acid sequence is shown in SEQ ID NO. 32.

71. The recombinant host according to claim 69 wherein said polypeptide comprises the amino acid sequence shown in SEQ ID NO. 32.

72. The recombinant host according to claim 69 wherein said amino acid sequence is shown in SEQ ID NO. 36.

73. The recombinant host according to claim 69 wherein said polypeptide comprises the amino acid sequence shown in SEQ ID NO. 36.

74. The recombinant host according to claim 69 wherein said amino acid sequence is shown in SEQ ID NO. 41.

75. The recombinant host according to claim 69 wherein said polypeptide comprises the amino acid sequence shown in SEQ ID NO. 41.

76. A recombinant host that express a polynucleotide encoding a pesticidal polypeptide wherein said polynucleotide comprises a nucleotide sequence shown in a sequence selected from the group consisting of SEQ ID NO. 31, SEQ ID NO. 35, and SEQ ID NO. 40, SEQ ID NO. 44, and fragments of the foregoing that are sufficient to encode a pesticidal polypeptide.

77. The recombinant host according to claim 76 wherein said polynucleotide comprises a pesticidal portion of the nucleotide sequence is shown in SEQ ID NO. 31.

78. The recombinant host according to claim 76 wherein said polynucleotide comprises the nucleotide sequence is shown in SEQ ID NO. 31.

79. The recombinant host according to claim 76 wherein said polynucleotide comprises a pesticidal portion of the nucleotide sequence is shown in SEQ ID NO. 35.

80. The recombinant host according to claim 76 wherein said nucleotide sequence is shown in SEQ ID NO. 35.

81. The recombinant host according to claim 76 wherein said polynucleotide comprises a pesticidal portion of the nucleotide sequence is shown in SEQ ID NO. 40.

82. The recombinant host according to claim 76 wherein said nucleotide sequence is shown in SEQ ID NO. 40.

83. The recombinant host according to claim 76 wherein said nucleotide sequence is shown in SEQ ID NO. 44.

84. A recombinant host that expresses a polynucleotide encoding a pesticidal toxin from a *Bacillus thuringiensis* isolate selected from the group consisting of PS149B1, having the identifying characteristics of NRRL B-21553; and PS167H2, having the identifying characteristics of NRRL B-21554.

85. The recombinant host according to claim 84 wherein said isolate is PS149B1, having the identifying characteristics of NRRL B-21553.

86. The recombinant host according to claim 84 wherein said isolate is PS167H2, having the identifying characteristics of NRRL B-21554.

87. The recombinant host according to claim 84 wherein said toxin is approximately 10–15 kDa.

88. The recombinant host according to claim 85 wherein said toxin is approximately 10–15 kDa.

89. The recombinant host according to claim 86 wherein said toxin is approximately 10–15 kDa.

90. A recombinant host that expresses a polynucleotide encoding an approximately 10–15 kDa pesticidal toxin from *Bacillus thuringiensis* isolate PS80 JJ1, having the identifying characteristics of NRRL B-18679.

91. A recombinant host transformed to express the polynucleotide of claim 11.

92. The recombinant host of claim 91 wherein said host is a plant.

93. The recombinant host of claim 46 wherein said host is a plant.

94. The recombinant host of claim 69 wherein said host is a plant.

95. The recombinant host of claim 76 wherein said host is a plant.

96. The recombinant host of claim 84 wherein said host is a plant.

97. The recombinant host of claim 90 wherein said host is a plant.

98. A transformed host cell expressing at least a first polynucleotide, which encodes a first polypeptide of approximately 10–15 kDa, and at least a second polynucleotide, which encodes a second polypeptide of approximately 40–50 kDa, wherein said first polynucleotide has at least one characteristic selected from the following group of characteristics:

(a) said polynucleotide encodes a polypeptide having an amino acid sequence shown in SEQ ID NO. 32;

(b) said polynucleotide encodes a polypeptide having an amino acid sequence shown in SEQ ID NO. 35;

(c) said polynucleotide encodes a polypeptide having an amino acid sequence shown in SEQ ID NO. 41;

(d) said polynucleotide comprises a nucleotide sequence shown in SEQ ID NO. 31;

(e) said polynucleotide comprises a nucleotide sequence shown in SEQ ID NO. 35;

(f) said polynucleotide comprises a nucleotide sequence shown in SEQ ID NO. 40;

(g) said polynucleotide comprises a nucleotide sequence shown in SEQ ID NO. 44;

(h) said polynucleotide encodes a toxin from PS80JJ1, having the identifying characteristics of NRRL B-18679;

(i) said polynucleotide encodes a toxin from PS149B1, having the identifying characteristics of NRRL B-21553; and (j) said polynucleotide encodes a toxin from PS167H2, having the identifying characteristics of NRRL B-21554;

and wherein said second polynucleotide has at least one characteristic selected from the following group of characteristics:

(k) said polynucleotide encodes a polypeptide having an amino acid sequence shown in SEQ ID NO. 11;

(l) said polynucleotide encodes a polypeptide having an amino acid sequence shown in SEQ ID NO. 38;

(m) said polynucleotide encodes a polypeptide having an amino acid sequence shown in SEQ ID NO. 43;

(n) said polynucleotide comprises a nucleotide sequence shown in SEQ ID NO. 45;

(o) said polynucleotide comprises a nucleotide sequence shown in SEQ ID NO. 10;

(p) said polynucleotide comprises a nucleotide sequence shown in SEQ ID NO. 37;

(q) said polynucleotide comprises a nucleotide sequence shown in SEQ ID NO. 42;

(r) said polynucleotide encodes a toxin from PS80JJ1, having the identifying characteristics of NRRL B-18679;

(s) said polynucleotide encodes a toxin from PS149B1, having the identifying characteristics of NRRL B-21553; and (t) said polynucleotide encodes a toxin from PS167H2, having the identifying characteristics of NRRL B-21554.

99. The transformed host cell of claim 98 wherein said cell is a plant cell.

100. The cell according to claim 98 wherein said first polynucleotide encodes a polypeptide having an amino acid sequence shown in SEQ ID NO. 32.

101. The cell according to claim 98 wherein said first polynucleotide encodes a polypeptide having an amino acid sequence shown in SEQ ID NO. 36.

102. The cell according to claim 98 wherein said first polynucleotide encodes a polypeptide having an amino acid sequence shown in SEQ ID NO. 41.

103. The cell according to claim 98 wherein said first polynucleotide comprises a nucleotide sequence shown in SEQ ID NO. 31.

104. The cell according to claim 98 wherein said first polynucleotide comprises a nucleotide sequence shown in SEQ ID NO. 35.

105. The cell according to claim 98 wherein said first polynucleotide comprises a nucleotide sequence shown in SEQ ID NO. 40.

106. The cell according to claim 98 wherein said first polynucleotide comprises a nucleotide sequence shown in SEQ ID NO. 44.

107. The cell according to claim 98 wherein said first polynucleotide encodes a toxin from PS80JJ1, having the identifying characteristics of NRRL B-18679.

108. The cell according to claim 98 wherein said first polynucleotide encodes a toxin from PS149B1, having the identifying characteristics of NRRL B-21553.

109. The cell according to claim 98 wherein said first polynucleotide encodes a toxin from PS167H2, having the identifying characteristics of NRRL B-21554.

110. The cell according to claim 98 wherein said second polynucleotide encodes a polypeptide having an amino acid sequence shown in SEQ ID NO. 11.

111. The cell according to claim 98 wherein said second polynucleotide encodes a polypeptide having an amino acid sequence shown in SEQ ID NO. 38.

112. The cell according to claim 98 wherein said second polynucleotide encodes a polypeptide having an amino acid sequence shown in SEQ ID NO. 43.

113. The cell according to claim 98 wherein said second polynucleotide comprises a nucleotide sequence shown in SEQ ID NO. 45.

114. The cell according to claim 98 wherein said second polynucleotide comprises a nucleotide sequence shown in SEQ ID NO. 10.

115. The cell according to claim 98 wherein said second polynucleotide comprises a nucleotide sequence shown in SEQ ID NO. 37.

116. The cell according to claim 98 wherein said second polynucleotide comprises a nucleotide sequence shown in SEQ ID NO. 42.

117. The cell according to claim 98 wherein said second polynucleotide encodes a toxin from PS80JJ1, having the identifying characteristics of NRRL B-18679.

118. The cell according to claim 98 wherein said second polynucleotide encodes a toxin from PS149B1, having the identifying characteristics of NRRL B-21553.

119. The cell according to claim 98 wherein said second polynucleotide encodes a toxin from PS167H2, having the identifying characteristics of NRRL B-21554.

* * * * *

UNITED STATES PATENT AND TRADEMARK OFFICE
CERTIFICATE OF CORRECTION

PATENT NO. : 6,127,180
DATED : October 3, 2000
INVENTOR(S) : Narva, et al.

It is certified that error appears in the above-identified patent and that said Letters Patent is hereby corrected as shown below:

Column 5, line 1: "SEQ ID NO. 19" should read --SEQ ID NO. 29--.

Column 13, line 31: "handlink" should read --handling--.

Column 13, line 49: "conentrage" should read --concentrate--.

Column 15, line 22: "$CaCl_2 \cdot H_2O$" should read --$CaCl_2 \cdot 2H_2O$--.

Column 19, line 16: "wit" should read --with--.

Column 19, line 29: "(Stragagene" should read --(Stratagene--.

Column 24, line 50: "closed" should read --cloned--.

Column 25, line 42: "et." should read --etc.--.

Column 25, line 67: "section" should read --selection--.

Column 26, line 11: "injection" should read --injection,--.

Column 26, line 48: "the manner" should read --the normal manner--.

UNITED STATES PATENT AND TRADEMARK OFFICE
CERTIFICATE OF CORRECTION

Page 2 of 2

PATENT NO. : 6,127,180
DATED : October 3, 2000
INVENTOR(S) : Narva, et al.

It is certified that error appears in the above-identified patent and that said Letters Patent is hereby corrected as shown below:

Column 72, line 19: "express" should read --expresses--.

Column 72, line 64: "PS80 JJ1" should read --PS80JJ1--.

Column 73, line 23: "SEQ ID NO. 35;" should read --SEQ ID NO. 36;--.

Signed and Sealed this

Eighth Day of May, 2001

Attest:

NICHOLAS P. GODICI

*Attesting Officer*   *Acting Director of the United States Patent and Trademark Office*